United States Patent

Woodle et al.

[11] Patent Number: 5,843,473
[45] Date of Patent: Dec. 1, 1998

[54] METHOD OF TREATMENT OF INFECTED TISSUES

[75] Inventors: Martin C. Woodle, Menlo Park, Calif.; Irma A.J.M. Bakker-Woudenberg, Bergschenhoek, Netherlands; Francis J. Martin, San Francisco, Calif.

[73] Assignee: SEQUUS Pharmaceuticals, Inc., Menlo Park, Calif.

[21] Appl. No.: 858,171

[22] Filed: Mar. 27, 1992

Related U.S. Application Data

[63] Continuation-in-part of Ser. No. 642,321, Jan. 15, 1991, Pat. No. 5,213,804, which is a continuation-in-part of Ser. No. 425,224, Oct. 20, 1989, Pat. No. 5,013,556.

[51] Int. Cl.⁶ .................................................. A61K 9/127
[52] U.S. Cl. .............................. 424/450; 514/78; 514/62
[58] Field of Search ........................... 514/78, 46, 42, 514/43, 53, 62; 424/450, 78.37, 78.31

[56] References Cited

U.S. PATENT DOCUMENTS

| | | | |
|---|---|---|---|
| 4,426,330 | 1/1984 | Sears | 264/403 |
| 4,501,728 | 2/1985 | Geho et al. | 424/38 |
| 4,534,899 | 8/1985 | Sears | 16/403 |
| 4,837,028 | 6/1989 | Allen | 424/450 |
| 4,885,172 | 12/1989 | Bally et al. | 424/417 |
| 4,904,479 | 2/1990 | Illum | 424/490 |
| 4,906,476 | 3/1990 | Radhakrishnan | 424/450 |
| 4,920,016 | 4/1990 | Allen et al. | 424/450 |
| 4,981,692 | 1/1991 | Popescu et al. | 424/422 |
| 5,013,556 | 5/1991 | Woodle et al. | 424/450 |
| 5,079,234 | 1/1992 | McGregor et al. | 424/78.31 |

FOREIGN PATENT DOCUMENTS

| | | |
|---|---|---|
| 0 072 111A1 | 7/1982 | European Pat. Off. |
| 0 118 316A3 | 3/1984 | European Pat. Off. |
| 0 354 355A2 | 8/1989 | European Pat. Off. |
| 63-76862 | 3/1988 | Japan |
| 2 185 397 | 1/1987 | United Kingdom |
| WO 88/04573 | 6/1988 | WIPO |
| WO 88/04924 | 7/1988 | WIPO |
| WO 90/04384 | 5/1990 | WIPO |

OTHER PUBLICATIONS

Bakker-Woudenberg, I.A.J.M., et al., "Biodistribution of Liposomes With Prolonged Circulation Time in Rats With *Klebsiella Pneumoniae* Lung Infection," Abstract in Liposomes in Drug Delivery: 21 Years On (1990).

Bakker-Woudenberg, I.A.J.M., et al., "Antibacterial Activity of Liposome-Entrapped Ampicillin in Vitro and in Vivo in Relation to the Lipid Composition," J. Pharmacol. Exp. Therap. 251:321–327 (1989).

Bermudez, L.E., et al., "Treatment of Disseminated *Mycobacterium avium* Complex Infection of Beige Mice with Liposome-Encapsulated Aminoglycosides," J. Infect. Dis. 161:1262–1268 (1990).

Fierer, J., et al., "Successful Treatment Using Gentamicin Liposomes of *Salmonella dublin* Infections in Mice," Antimicrob. Agents and Chemother.34(2):343–348 (1990).

Illum, L., and Davis, S.S., "Targeting of Colloidal Particles to the Bone Marrow," Life Sciences 40:1553–1560 (1987).

(List continued on next page.)

*Primary Examiner*—Neil Levy
*Attorney, Agent, or Firm*—Carol A. Stratford; Peter J. Dehlinger

[57] ABSTRACT

A method of treating a site of systemic infection which includes administering a therapeutic compound entrapped in liposomes. Also included is a liposomal composition and a method of preparing a liposomal composition for use in concentrating a therapeutic compound to an infected region via the bloodstream. The liposomes, which contain the agent in entrapped form, are composed of vesicle-forming lipids, a vesicle-forming lipid derivatized with hydrophilic biocompatible polymer, and have sizes in a selected size range between 0.07 and 0.2 microns. After parenteral administration, the liposomes are selectively taken up by the infected region within 24–48 hours, for release of entrapped compound into the infected region.

5 Claims, 13 Drawing Sheets

OTHER PUBLICATIONS

Illum, L., and Davis., S.S., "Effect of the Nonionic Surfactant Poloxamer 338 on the Fate and Deposition of Polystyrene Microspheres Following Intravenous Administration," J. Pharmaceut. Sci. 72(9):1086–1089 (1983).

Illum, L., et al., "The Organ Distribution and Circulation Time of Intravenously Injected Colloidal Carriers Sterically Stabilized with a Blockcopolymer—Poloxamine 908," Life Sciences 40:367–374 (1987).

Illum, L., and Davis, S.S., "The organ uptake of intravenously administered colloidal particles can be altered using a nonionic surfactant (Poloxamer 338)," FEBS Letters 167(1):79–82 (1984).

Papahadjopoulos, D., et al., "Sterically stabilized liposomes: Improvements in pharmacokinetics and antitumor therapeutic efficacy," Proc. Natl. Acad. Sci. USA 88:11460–11464 (1981).

Poste, G., et al., "The Challenge of Liposome Targeting in Vivo," in *Liposome Technology Vol. III: Targeted Drug Delivery and Biological Interaction*, G. Gregoriadis, ed., CRC Press, Boca Raton (1984): Chapter 1, pp. 1–28.

Poznansky, M.J., and Juliano, R.L., "Biological Approaches to the Controlled Delivery of Drugs: A Critical Review," Pharmacol. Reviews 36(4):278–336 (1984).

Tomlinson, E., "Strategies for Achieving Site–Specific Drug Delivery," DN&P 2(1):5–14 (1989).

Woodle, M.C., et al., "Improved Long Circulating (Stealth®) Liposomes Using Synthetic Lipids," Proceed. Intern. Symp. Control Rel. Bioact. Mater 17:77–78 (1990).

Woodle, M.C., et al., "In vivo studies of long circulating (Stealth®) liposomes in rats," Period. Biol. 93:349–352 (1991).

Woodle, M.C., et al., "Prolonged Systemic Delivery of Peptide Drugs by Long–Circulating Liposomes: Illustration with Vasopressin in the Brattleboro Rat," Pharm. Res. 9:260–265 (1992).

METHOD OF TREATMENT OF INFECTED TISSUES

This application is a continuation-in-part of application Ser. No. 642,321, filed Jan. 15, 1991, now U.S. Pat. No. 5,213,804 which is a continuation-in-part of U.S. patent application Ser. No. 425,224, now U.S. Pat. No. 5,013,556, filed Oct. 20, 1989.

FIELD OF THE INVENTION

The present invention relates to a liposome composition position and method, particularly for use in concentrating therapeutics at sites of tissue infection, such as is caused by a bacterial invasion.

REFERENCES

Allen, T. M., (1981) Biochem. Biophys. Acta 640. 385397.

Allen, T. M., and Everest, J. (1983) J. Pharmacol. Exp. Therap. 226. 539–544.

Altura, B. M. (1980) Adv. Microcirc. 9, 252–294.

Alving, C. R. (1984) Biochem. Soc. Trans. 12. 342344.

Ashwell, G., and Morell, A. G. (1974) Adv. Enzymology 41, 99–128.

Bakker-Woudenberg, I. J. M. et al., (1990) Liposomes in Drug Delivery: 21 Years on (Abstract).

Bartlett, G. R. (1959) J. Biol. Chem. 234:466–468.

Czop, J. K. (1978) Proc. Natl. Acad. Sci. U.S.A. 75:3831.

Durocher, J. P., et al. (1975) Blood 45:11.

Ellens, H., et al. (1981) Biochim. Biophys. Acta 674. 10–18.

Fierer, J., Hatlin, L., Lin, J.-P., Estrella, D., Mihalko, P., and Yau-Young, A. (1990) Antimicrob. Agents and Chemother. 34: 343–348.

Gabizon, A., Goren, D. and Barenholz, Y. (1988) Israel J. Med. Sci. 24, 512–517.

Gabizon, A., Huberty, J., Straubinger, R. M., Price, D. C. and Papahadjopoulos, D. (1988–1989) J. Liposome Resh. 1, 123–135.

Gabizon, A., Shiota, R. and Papahadjopoulos, D. (1989) J. Natl. Cancer Inst. 81, 1484–1488.

Gilman, A. G. et al. (1990) *Goodman and Gilman's The Pharmacological Basis of Therapeutics* Eighth Edition, Pergamon Press, New York.

Gregoriadis, G., and Ryman, B. E. (1972) Eur. J. Biochem. 24. 485–491.

Gregoriadis, G., and Neerunjun, D. (1974) Eur. J. Biochem. 47, 179–185.

Gregoriadis, G., and Senior, J. (1980) FEBS Lett. 119, 43–46.

Greenberg, J. P., et al.(1979) Blood 53:916.

Hakomori, S. (1981) Ann. Rev. Biochem. 50:733–764.

Heaton, W. A., Davis, H. H., Welch, M. J., Mathias, C. J., Joist, J. H., Sherman, L. A. and Siegel, B. A. (1979) Br. J. Haematol. 42:613–622.

Hong, K., Friend, D., Glabe, C. and Papahadjopoulos (1984) Biochem. Biophys. Acta 732:320–323.

Hwang, K. J., et al. (1980) Proc. Natl. Acad. Sci. U.S.A. 77:4030.

Jain, K. J. (1989) J. Natl. Can. Inst. 81, 570–576.

Jonah, M. M., et al. (1975) Biochem. Biophys. Acta 401, 336–348.

Juliano, R. L., and Stamp, D. (1975) Biochem. Biophys. Res. Commun. 63. 651–658.

Karlsson, K. A. (1982) In: Biological Membranes, Vol. 4, D. Chapman (ed.) Academic Press, New York, pp. 1–74.

Kimelberg, H. K., et al. (1976) Cancer Res. 36,2949–2957.

Kirby, C. J. and Gregoriadis (1984) In: Liposome Technology, Vol. 3, G. Gregoriadis (ed.) CRC Press, Boca Raton, Fla., p. 19.

Lee, K. C., et al., J. Immunology 125:86 (1980).

Lopez-Berestein, G., et al. (1984) Cancer Res. 44, 375–378.

Martin, F. J. (1990) In: Specialized Drug Delivery Systems—Manufacturing and Production Technology, P. Tyle (ed.) Marcel Dekker, New York, pp. 267–316.

Okada, N. (1982) Nature 299:261.

Papahadjopoulos, D., et al., Sterically Stabilized Liposomes: Improvements in Pharmacokinetics and Anti-Tumor Therapeutic Efficacy, PNAS (1991) in press.

Poste, G., et al., in "Liposome Technology" Volume 3, page 1 (Gregoriadis, G., et al, eds.), CRC Press, Boca Raton (1984).

Poznansky, M. J., and Juliano, R. L. (1984) Pharmacol. Rev. 36. 277–336.

Richardson, V. J., et al. (1979) Br. J. Cancer 40, 3543.

Saba, T. M. (1970) Arch. Intern. Med. 126. 1031–1052.

Schaver, R. (1982) Adv. Carbohydrate Chem. Biochem. 40:131.

Scherphof, T., et al. (1978) Biochim. Biophys. Acta 542, 296–307.

Senior, J., and Gregoriadis, G. (1982) FEBS Lett. 145, 109–114.

Senior, J., et al. (1985) Biochim. Biophys. Acta 839, 1–8.

Storm, G., Roerdintz, Steerenberg, P. A. de Jong, W. H. and Crommelin, D. J. A. (1987) Can. Res. 47, 3366–3372.

Szoka, F., Jr., et al. (1978) Proc. Natl. Acad. Sci. U.S.A. 75:4194.

Szoka, F., Jr., et al. (1980) Ann. Rev. Biophys. Bioeng. 9:467.

Tice, T. R., et al., (1984) Pharmaceutical Technology, November 1984, pp. 26–35.

Weinstein, J. W., et al., Pharmac Ther, 24:207 (1984).

Weise, D. L., et al., in Drug Carriers in Biology and Medicine, G. Gregoriadis, Ed.—Academic Press, New York, 1979, pp. 237–270.

Woodle, M. C., et al., (1990). Improved long circulating (Stealth®) Liposomes using synthetic liposomes. Proceed. Intern. Symp. Control. Rel. Bioact. Mater., 17:77.

Woodle, M. C., et al., (1991). In vivo Studies of Long Circulating (Stealth®) Liposomes in Rats, Period Biol., 93:349.

Woodle, M. C. et al. (1992) Pharm. Res. 9:260–265.

Woodruff, J. J., et al. (1969) J. Exp. Med. 129:551.

BACKGROUND OF THE INVENTION

Currently available treatment regimens for treatment of infected tissues or regions, prescribe systemic administration of antimicrobial compounds, when such tissues are not readily accessible to topical administration. It would be desirable to target therapeutic compounds selectively to such infected regions via the bloodstream, in order to reduce toxic side effects and to increase the drug dose which can safely be delivered to an infected region, while sparing other body regions from exposure to such compounds.

Liposomes have been proposed as a drug carrier for intravenously (IV) administered compounds, including both imaging and therapeutic compounds. However, the use of liposomes for site-specific targeting via the bloodstream has been severely restricted by the rapid clearance of liposomes by cells of the reticuloendothelial system (RES). Typically, the RES will remove 80–95% of a dose of IV injected liposomes within one hour, effectively out-competing the selected target site for uptake of the liposomes. Liposomal treatment of infections has therefore been largely limited to treatment of the reticuloendothelial system (Fierer).

RES uptake of liposomes has been reported to be influenced by a variety of factors (e.g., Gregoriadis, 1974; Jonah; Gregoriadis, 1972; Juliano; Allen, 1983; Kimelberg, 1976; Richardson; Lopez-Berestein; Allen, 1981; Scherphof; Gregoriadis, 1980; Hwang; Patel, 1983; Senior, 1985; Allen, 1983; Ellens; Senior, 1982; Hwang; Ashwell; Hakomori; Karlsson; Schauer; Durocher; Greenberg; Woodruff; Czop; and Okada). Briefly, liposome size, charge, degree of lipid saturation, and surface moieties have all been implicated in liposome clearance by the RES. However, no single factor identified to date has been effective to provide long blood halflife, and more particularly, a relatively high percentage of liposomes in the bloodstream 24 hours after injection.

In addition to a long blood halflife, effective drug delivery to an infected site via the bloodstream would also require that the liposomes be capable of penetrating the continuous endothelial cell layer and underlying basement membrane surrounding the vessels supplying blood to the region. Local infection is accompanied by an acute increase in permeability of the vasculature to proteins in the region of the infection, followed by migration of neutrophils out of the bloodstream into the infected region. However, neither of these events predicts the ability of liposomes to pass through epithelial cell barriers and adjacent basement membrane, since proteins are generally much smaller than liposomes, and neutrophils possess specific binding sites and active mechanisms for penetrating the blood vessels.

In fact, studies reported to date indicate that even where the permeability of blood vessels increases, extravasation of conventional liposomes through the vessels does not increase significantly (Poste). Based on these findings, it was concluded that although extravasation of liposomes from capillaries compromised by disease may be occurring on a limited scale below detection levels, its therapeutic potential would be minimal (Poste).

SUMMARY OF THE INVENTION

One general object of the invention is to provide a liposome composition and method which is effective for treating an infection localized at a site other than the fixed macrophages residing in the liver or spleen, by concentrating the liposomes, and thereby a therapeutic compound, in the infected region.

The invention includes, in one aspect, a method of treating a site of systemic infection which is localized at a tissue site as described above. The method includes parenteral injection of a composition of liposomes which (i) are composed of vesicle-forming lipids including an amphipathic vesicle-forming lipid derivatized with a hydrophilic biocompatible polymer of a size and molecular weight effective to extend the liposome blood circulation time several-fold over that of liposomes lacking such a lipid-derivatized hydrophilic polymer, (ii) have a selected mean particle diameter in the size range between about 0.07–0.20 microns, and (iii) contain in liposome-entrapped form, a therapeutic compound effective against the source of the infection. Injection of this composition is effective to concentrate the liposomes in the infected region, thereby concentrating the therapeutic compound in the infected tissue.

In a preferred embodiment, the hydrophilic polymer is polyethylene glycol having a molecular weight between about 300 and 5,000 daltons. In another preferred embodiment, the hydrophilic polymer is selected from the group consisting of polyglycolic acid (PGA), polylactic acid (PLA), a copolymer of PGA and PLA, and polyvinyl alcohol (PVA).

Liposome entrapped therapeutic compounds are preferably antimicrobial or anti-infective agents, including antibiotic, antifungal, antiviral, anthelminthic, and anti-parastic agents. For use in a bacterial infection, the therapeutic compound is preferably an antibiotic. In a preferred embodiment, at least about 60% of the antibiotic agent is in liposome-entrapped form. In another preferred embodiment, the antibiotic agent is an aminoglycoside antibiotic, and it is present entrapped in the liposomes at a concentration greater than 20 $\mu$g compound/$\mu$mole liposome lipid.

In a preferred embodiment, the method is used to treat Klebsiella infection of the lung with gentamicin. The treatment method may also be used in the treatment of Aspergillus infection of the lung with an antifungal such as amphotericin B, treatment of Bacteroides infections, such as of the lung, bowel, brain or pelvis with clindamycin, a penicillin, a cephalosporin, metronidazole, or chloramphenicol, treatment of Pseudomonas infection of the prostate with a broad spectrum penicillin, or treatment of staphyllococcal endocarditis or osteomyelitis with vancomycin, a penicillin, or a cephalosporin. In addition, according to the invention, certain viral dermal infections, such as herpes infections, may be treated using systemic administration of a liposomal composition of acyclovir. Treatment of infections residing in liver hepatocytes may be treated, according to the method of the invention. Specifically, hepatitis B or C may be treated with liposomal compositions of a DNA polymerase inhibitor, such as zidovudine. Additionally, the treatment method may be used for systemic treatment of certain infections of the central nervous system, when the blood brain barrier is rendered permeable by such an infection. Examples include treatment of meningitis due to Pneumococcus, Pseudomonas, Listeria, or Meningococcus by a penicillin, a cephalosporin, erythromycin, or gentamicin, treatment of meningitis caused by Cryptococcus by amphotericin or fluconazole, and treatment of meningitis due to Hemophilus influenzae or Streptococcus pneumoniae by penicillins, cephalosporins, or chloramphenicol.

In a related aspect, the invention also includes an injectable liposome composition for use in a method of treating a site of systemic infection which is localized at a tissue site other than the fixed macrophage cells of the liver or the spleen. The composition includes liposomes composed of vesicle-forming lipids including an amphipathic vesicle-forming lipid derivatized with a hydrophilic biocompatible polymer, as described above. The liposomes of the composition also have a selected mean particle diameter in the size range between about 0.07–0.20 microns, and contain, in liposome-entrapped form, a therapeutic compound effective against the source of the infection. Such liposomes accumulate selectively in the infected tissue to concentrate the therapeutic compound in the infection site.

In a preferred embodiment, the hydrophilic polymers of the composition is a polyethyleneglycol having a molecular weight between about 300–5,000 daltons. In another preferred embodiment, the hydrophilic polymer of the composition is selected from the group consisting of PGA, PLA, a copolymer of PGA and PLA, and PVA. In another preferred embodiment, the composition of the invention includes an aminoglycoside antibiotic. In still another preferred embodiment, the composition includes gentamicin and is used for treatment of an infection in the lung.

In another related aspect, the invention includes a method of preparing an anti-infective or antimicrobial agent for localization in an infected region of tissue by intravenous injection. The method includes entrapping the agent in a liposome-composition as described above.

These and other objects and features of the present invention will become more fully apparent when the following detailed description of the invention is read in conjunction with the accompanying drawings.

DETAILED DESCRIPTION OF THE INVENTION

I. Preparation of Derivatized Lipids

Figure 1:
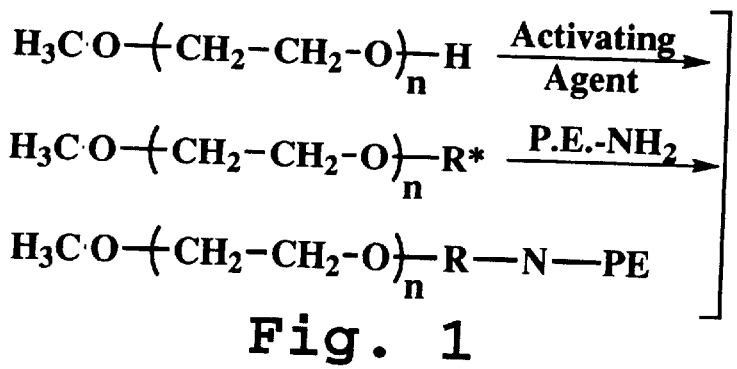
FIG. 1 illustrates a general reaction scheme for derivatizing a vesicle-forming lipid amine with a polyalkylether.

FIG. 1 shows a general reaction scheme for preparing a vesicle-forming lipid derivatized with a biocompatible, hydrophilic polymer, as exemplified by polyethylene glycol (PEG), polylactic acid (PLA), polyglycolic acid (PGA) and polyvinyl alcohol (PVA). These polymers are readily water soluble, can be coupled to vesicle-forming lipids, and are tolerated in vivo without toxic effects. The hydrophilic polymer which is employed, e.g., PEG, is preferably capped by a methoxy, ethoxy or other unreactive group at one end or, alternatively, has a chemical group that is more highly reactive at one end than the other. The polymer is activated at one of its ends by reaction with a suitable activating agent, designated R* in the figure, such as cyanuric acid, diimadozle, anhydride reagent, or the like, as described below. The activated compound is then reacted with a vesicle-forming lipid, such as a diacyl glycerol, including diacyl phosphoglycerols, where the two hydrocarbon chains are typically between 14–22 carbon atoms in length and have varying degrees of saturation, to produce the derivatized lipid. Phosphatidylethanolamine (PE) is an example of a phospholipid which is preferred for this purpose since it contains a reactive amino group which is convenient for coupling to the activated polymers. Alternatively, the lipid group may be activated for reaction with the polymer, or the two groups may be joined in a concerted coupling reaction, according to known coupling methods. PEG capped at one end with a methoxy or ethoxy group can be obtained commercially in a variety of polymer sizes, e.g., 500–20,000 dalton molecular weights.

The vesicle-forming lipid is preferably one having two hydrocarbon chains, typically acyl chains, and a polar head group. Included in this class are the phospholipids, such as phosphatidylcholine (PC), PE, phosphatidic acid (PA), phosphatidylinositol (PI), and sphingomyelin (SM), where the two hydrocarbon chains are typically between about 14–22 carbon atoms in length, and have varying degrees of unsaturation. Also included in this class are the glycolipids, such as cerebrosides and gangliosides.

Another vesicle-forming lipid which may be employed is cholesterol and related sterols. In general, cholesterol may be less tightly anchored to a lipid bilayer membrane, particularly when derivatized with a high molecular weight polymers, such as polyalkylether, and therefore be less effective in promoting liposome evasion of the RES in the bloodstream.

More generally, and as defined herein, "vesicle-forming lipid" is intended to include any amphipathic lipid having hydrophobic and polar head group moieties, and which (a) by itself can form spontaneously into bilayer vesicles in water, as exemplified by phospholipids, or (b) is stably incorporated into lipid bilayers in combination with phospholipids, with its hydrophobic moiety in contact with the interior, hydrophobic region of the bilayer membrane, and its polar head group moiety oriented toward the exterior, polar surface of the membrane. An example of a latter type of vesicle-forming lipid is cholesterol and cholesterol derivatives, such as cholesterol sulfate and cholesterol hemisuccinate.

According to one important feature of the invention, the vesicle-forming lipid may be a relatively fluid lipid, typically meaning that the lipid phase has a relatively low liquid to liquid-crystalline melting temperature, e.g., at or below room temperature, or relatively rigid lipid, meaning that the lipid has a relatively high melting temperature, e.g., up to 60° C. As a rule, the more rigid, i.e., saturated, lipids contribute to greater membrane rigidity in a lipid bilayer structure and also contribute to greater bilayer stability in serum. Other lipid components, such as cholesterol, are also known to contribute to membrane rigidity and stability in lipid bilayer structures. As mentioned above, a long chain (e.g. C-18) saturated lipid plus cholesterol is one preferred composition for delivering therapeutics to infected sites, since these liposomes do not tend to release the drugs into the plasma as they circulate through the bloodstream and enter the infected region during the first 48 hours following injection. Phospholipids whose acyl chains have a variety of degrees of saturation can be obtained commercially, or prepared according to published methods.

According to another important feature of the invention, the vesicle-forming lipid includes an amphipathic vesicle-forming lipid having a derivatized hydrophilic biocompatible polymer. In experiments in support of the invention, and as noted below, it has been found that the presence of such polymers derivatized to vesicle-forming lipids in liposomal compositions is effective to significantly enhance liposome blood circulation time, in comparison to liposomes formed from lipids in the absence of such derivatized hydrophilic polymers.

It will be appreciated that the polymer-derivatized lipids must be (a) safe for parenteral administration, both in terms of toxicity, biodegradability, and tissue compatibility, (b) compatible with stable lipid bilayer formation and structure, and (c) amenable to liposome preparation and processing steps. These requirements are met by PEG polymers which have been approved for human use in the U.S., and also by the thermoplastic polyester polymers polylactic acid and polyglycolic acid (also referred to as polylactide and polyglycolide), copolymers of lactide and glycolide, such as poly(lactide-co-glycolide), and polyvinyl alcohols. In particular, the polyester polymers are safe to administer because they biodegrade by undergoing random, nonenzymatic, hydrolytic cleavage of their ester linkages to form lactic acid and glycolic acid, which are normal metabolic compounds (Tice and Cowsar, and Weise et al.).

Figure 2:
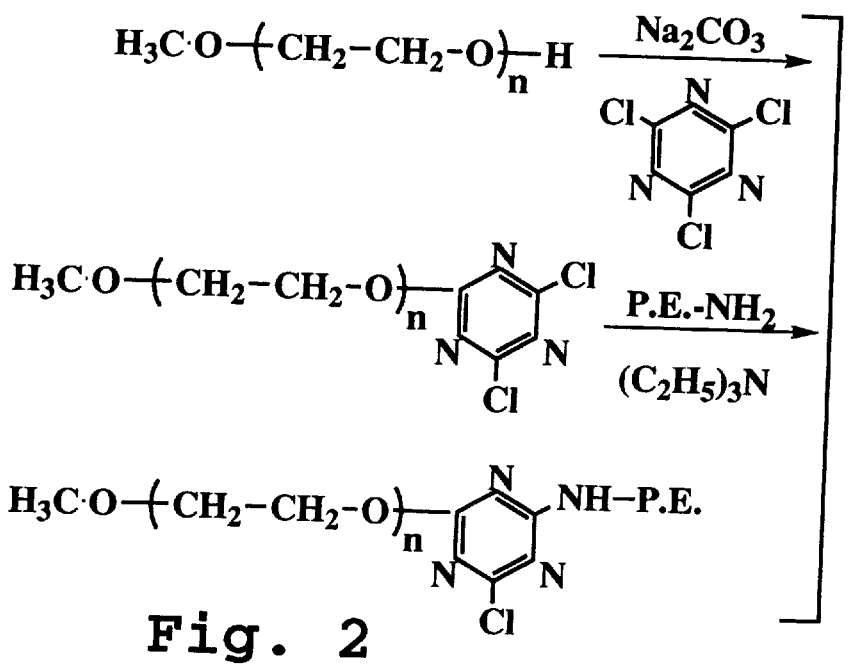
FIG. 2 is a reaction scheme for preparing phosphatidylethanolamine (PE) derivatized with polyethyleneglycol via a cyanuric chloride linking agent.

FIG. 2 shows a reaction scheme for producing a PE-PEG lipid in which the PEG is derivatized to PE through a cyanuric chloride group. Details of the reaction are provided in Example 1. Briefly, methoxy-capped PEG is activated with cyanuric chloride in the presence in sodium carbonate under conditions which produced the activated PEG compound shown in the figure. This material is purified to remove unreacted cyanuric acid. The activated PEG compound is reacted with PE in the presence of triethyl amine (TEA) to produce the desired PE-PEG compound shown in the figure. The yield is about 8–10% with respect to initial quantities of PEG.

The method just described may be applied to a variety of lipid amines, including PE, cholesteryl amine, and glycolipids with sugar-amine groups.

Figure 3:
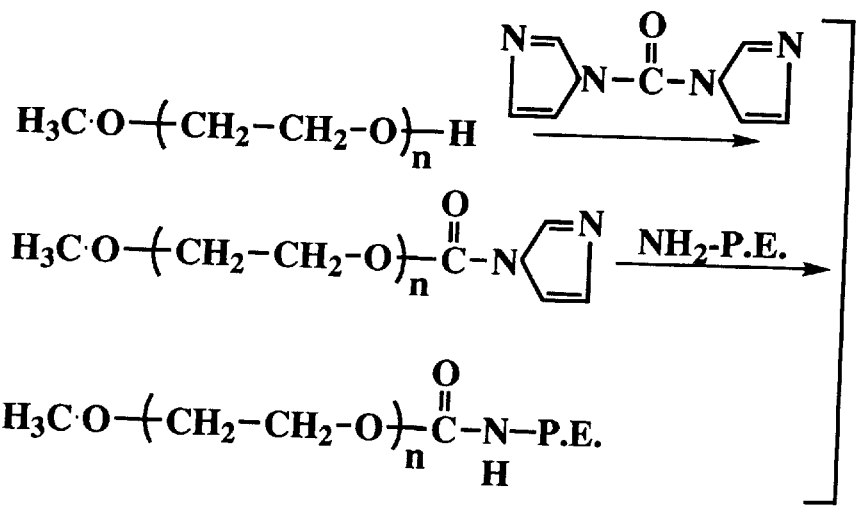
FIG. 3 illustrates a reaction scheme for preparing phosphatidylethanolamine (PE) derivatized with polyethyleneglycol by means of a diimidazole activating reagent.

A second method of coupling a polyalkylether, such as capped PEG to a lipid amine is illustrated in FIG. 3. Here the capped PEG is activated with a carbonyl diimidazole (CDI) coupling reagent, to form the activated imidazole compound shown in FIG. 3. Reaction with a lipid amine, such as PE leads to PEG coupling to the lipid through an amide linkage, as illustrated in the PEG-PE compound shown in the figure. Details of the reaction are given in Example 2.

Figure 4:
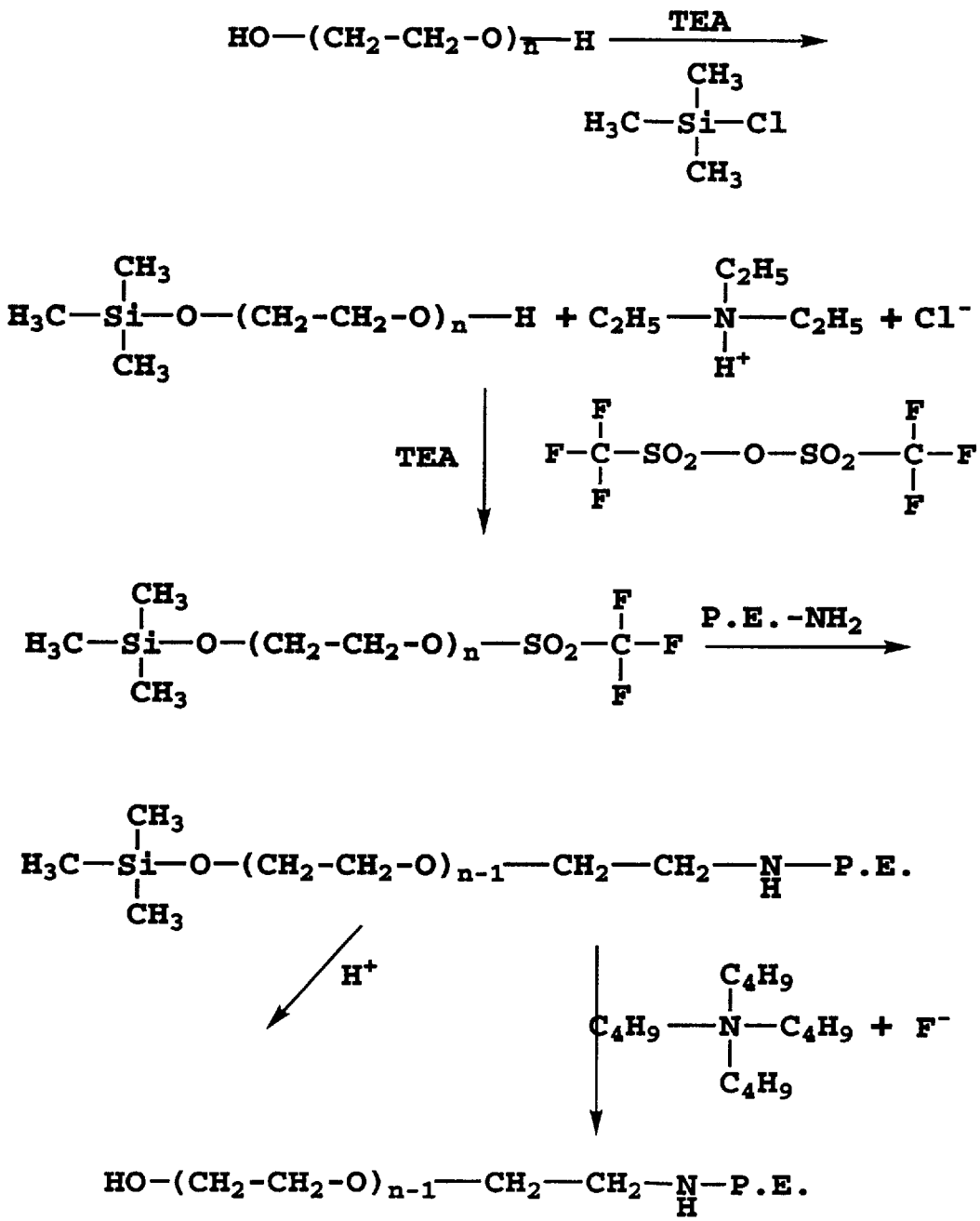
FIG. 4 illustrates a reaction scheme for preparing phosphatidylethanolamine (PE) derivatized with polyethyleneglycol by means of a trifluoromethane sulfonate reagent.

A third reaction method for coupling a capped polyalkylether to a lipid amine is shown in FIG. 4. Here PEG is first protected at its OH end by a trimethylsilane group. The end-protection reaction is shown in the figure, and involves the reaction of trimethylsilylchloride with PEG in the presence of triethylamine (TEA). The protected PEG is then reacted with the anhydride of trifluoromethyl sulfonate to form the PEG compound activated with trifluoromethyl sulfonate. Reaction of the activated compound with a lipid amine, such as PE, in the presence of triethylamine, gives the desired derivatized lipid product, such as the PEG-PE compound, in which the lipid amine group is coupled to the polyether through the terminal methylene carbon in the polyether polymer. The trimethylsilyl protective group can be released by acid treatment, as indicated in the figure, or, alternatively, by reaction with a quaternary amine fluoride salt, such as the fluoride salt of tetrabutylamine.

It will be appreciated that a variety of known coupling reactions, in addition to those just described, are suitable for preparing vesicle-forming lipids derivatized with hydrophilic polymers such as PEG, polylactic acid, polyglycolic acid, polylactic-polyglycolic copolymers and polyvinyl alcohol. For example, the sulfonate anhydride coupling reagent illustrated in FIG. 4 can be used to join an activated polyalkylether to the hydroxyl group of an amphipathic lipid, such as the 5'-OH of cholesterol. Other reactive lipid groups, such as an acid or ester lipid group may also be used for coupling, according to known coupling methods. For example, the acid group of phosphatidic acid can be activated to form an active lipid anhydride, by reaction with a suitable anhydride, such as acetic anhydride, and the reactive lipid can then be joined to a protected polyalkylamine by reaction in the presence of an isothiocyanate reagent.

Figure 5A:
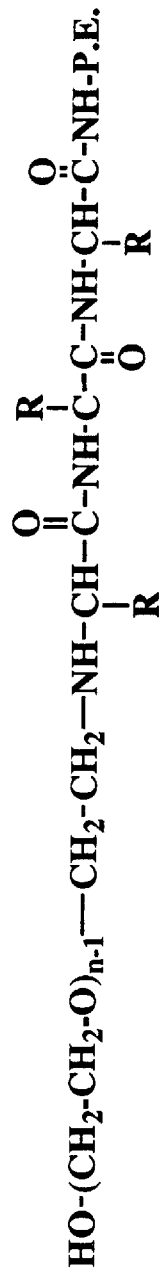
FIG. 5 illustrates a vesicle-forming lipid derivatized with polyethyleneglycol through a peptide (5A), ester (5B), and disulfide (5C) linkage.
Figure 5B:
Figure 5C:

In another embodiment, the derivatized lipid components are prepared to include a labile lipid-polymer linkage, such as a peptide, ester, or disulfide linkage, which can be cleaved under selective physiological conditions, such as in the presence of peptidase or esterase enzymes or reducing agents such as glutathione present in the bloodstream. FIG. 5 shows exemplary lipids which are linked through (5A) peptide, (5B) ester, and (5C) disulfide containing linkages. The peptide-linked compound can be prepared, for example, by first coupling a polyalkylether with the N-terminal amine of the tripeptide shown, e.g., via the reaction shown in FIG. 3. The peptide carboxyl group can then be coupled to a lipid amine group through a carbodiimide coupling reagent conventionally. The ester linked compound can be prepared, for example, by coupling a lipid acid, such as phosphatidic acid, to the terminal alcohol group of a polyalkylether, using alcohol via an anhydride coupling agent. Alternatively, a short linkage fragment containing an internal ester bond and suitable end groups, such as primary amine groups can be used to couple the polyalkylether to the amphipathic lipid through amide or carbamate linkages. Similarly, the linkage fragment may contain an internal disulfide linkage, for use in forming the compound shown in FIG. 5C. Polymers coupled to phospholipids via such reversible linkages are useful to provide high blood levels of liposomes which contain them for the first few hours post injection. After this period, plasma components cleave the reversible bonds releasing the polymers and the "unprotected" liposomes are rapidly taken up by the RES by the same mechanism as conventional liposomes.

Figure 6:
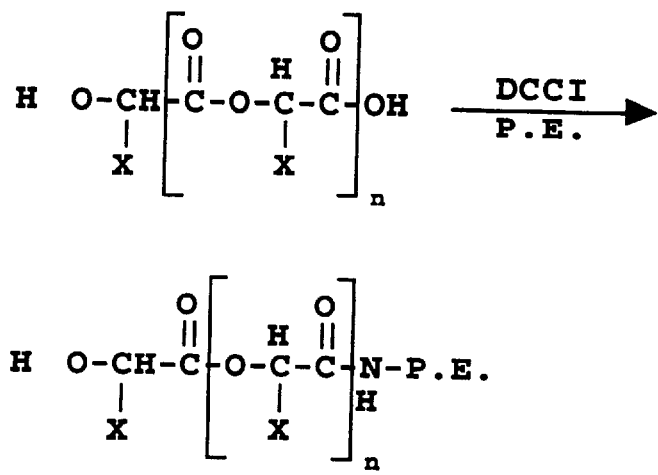
FIG. 6 illustrates a reaction scheme for preparing phosphatidylethanolamine (PE) derivatized with polylactic acid (PLA), polyglycolic acid (PGA), and copolymers of the two.

FIG. 6 illustrates a method for derivatizing polylactic acid, polyglycolic acid and polylactic-polyglycolic acid copolymers with PE in an amide linkage. The polylactic acid is reacted, in the presence of PE, with dicyclohexylcarboimide (DCCI), as detailed in Example 2. Similarly, a vesicle-forming lipid derivatized with polyglycolic acid may be formed by reaction of polyglycolic acid or glycolic acid with PE in the presence of a suitable coupling agent, such as DCCI, also as detailed in Example 2. Similar chemistry may be used to form lipid derivatives of polylactic-polyglycolic acid copolymers. Polyvinyl alcohol (PVA) is similarly derivatized with PE to form a carbamate linkage, as detailed in Example 2, by first reaching PE with carbonyl diimidazole (CDI), followed by addition of a low molecular weight fraction of PVA in the presence of triethylamine. The vesicle-forming lipids derivatized with either polylactic acid or polyglycolic acid and their copolymers or polyvinyl alcohol form part of the invention herein. Also forming part of the invention are liposomes containing these derivatized lipids.

II. Preparation of Liposomes

A. Lipid Components

The lipid components used in forming the liposomes of the invention may be selected from a variety of vesicle-forming lipids, typically including phospholipids, sphingolipids and sterols. As will be seen, one requirement of the liposomes of the present invention is long blood circulation lifetime. It is therefore useful to establish a standardized measure of blood lifetime which can be used for evaluating the effect of lipid components on blood halflife.

One method used for evaluating liposome circulation time in vivo measures the distribution of IV injected liposomes in the bloodstream and the primary organs of the RES at selected times after injection. In the standardized model which is used herein, RES uptake is measured by the ratio of total liposomes in the bloodstream to total liposomes in the liver and spleen, the principal organs of the RES. It should be noted that although uptake in such tissues is specifically into RES cells, the fixed macrophages of the liver and spleen, evaluation of RES uptake is conventionally carried out by measuring total uptake by the whole tissues. Thus, when stated herein that RES uptake was measured in the liver and spleen, it is understood that such uptake was primarily by the fixed macrophages of the liver and spleen. In practice, age and sex matched rats or mice are injected IV through the tail vein with a radiolabeled liposome composition, and each time point is determined by measuring total blood and combined liver and spleen radiolabel counts, as detailed in Example 5.

Since the liver and spleen, and specifically, the fixed macrophages in the liver and spleen, account for nearly 100% of the initial uptake of liposomes by the RES, the blood/RES ratio just described provides a good approximation of the extent of uptake from the blood to the RES in vivo. For example, a ratio of about 1 or greater indicates a predominance of injected liposomes remaining in the bloodstream, and a ratio below about 1, a predominance of liposomes in the RES. For most of the lipid compositions of interest, blood/RES ratios were calculated at 1, 2, 3, 4, and 24 hours post injection.

The liposomes of the present invention include a vesicle-forming lipid derivatized with a hydrophilic polymer, described in Section I. According to one aspect of the invention, it has been discovered that blood circulation half-lives in these liposomes are largely independent of the degree of saturation of the phospholipid components making up the liposomes. That is, the phospholipid components may be composed predominantly of fluidic, relatively unsaturated, acyl chains, or of more saturated, rigidifying acyl chain components. This feature of the invention is seen in Example 6, which examines blood/RES ratios in liposomes formed with PEG-PE, cholesterol, and PC having varying degrees of saturation (Table 4). As seen from the data in Table 5 in the example, high blood/RES ratios were achieved in substantially all of the liposome formulations, independent of the extent of lipid unsaturation in the bulk PC phospholipid, and no systematic trend, as a function of degree of lipid saturation, was observed.

Accordingly, the vesicle-forming lipids may be selected to achieve a selected degree of fluidity or rigidity, to control the stability of the liposomes in serum and the rate of release of entrapped drug from the liposomes in the bloodstream and/or infected region. The vesicle-forming lipids may also be selected, in lipid saturation characteristics, to achieve desired liposome preparation properties. It is generally the case, for example, that more fluidic lipids are easier to formulate and down-size by extrusion and homogenization methods than more rigid lipid compositions.

Figure 18A:
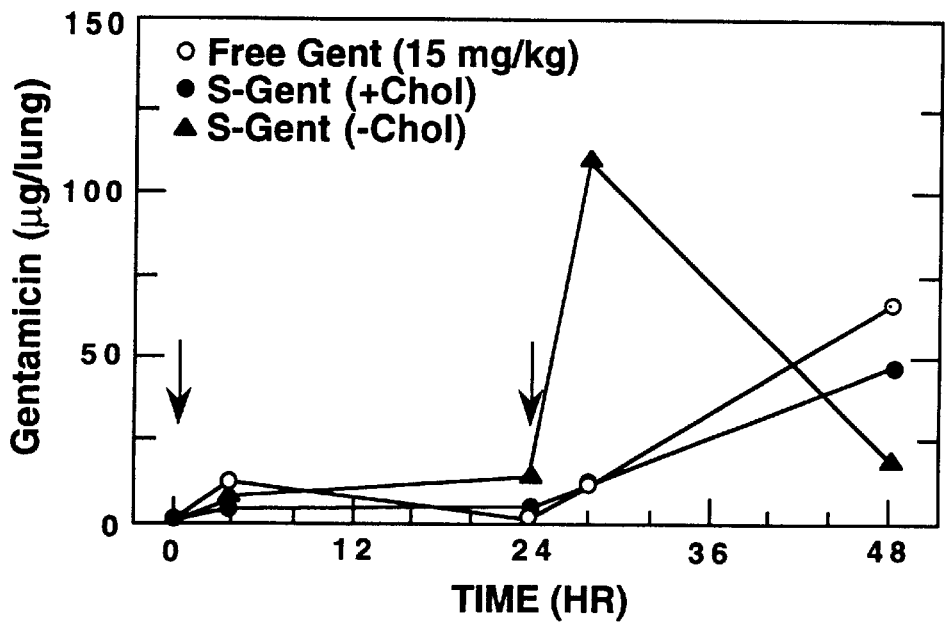
FIG. 18A shows a plot of the time course of gentamicin accumulation ($\mu$g/lung) in rat lungs infected at time=0 with $K.$ $pneumoniae$ and treated at time=24 hours with gentamicin sulfate (15 mg/kg; open circles), gentamicin sulfate-loaded PEG-containing liposomes having a composition of PEG-DSPE:PC:Chol=0.15:1.85:1 (1.9 mg gentamicin/kg; solid circles), or gentamicin sulfate-loaded PEG-containing, cholesterol-free liposomes having a composition of PEG-DSPE:PC=0.15:2.85 (1.9 mg gentamicin/kg; solid triangles)
Figure 18B:
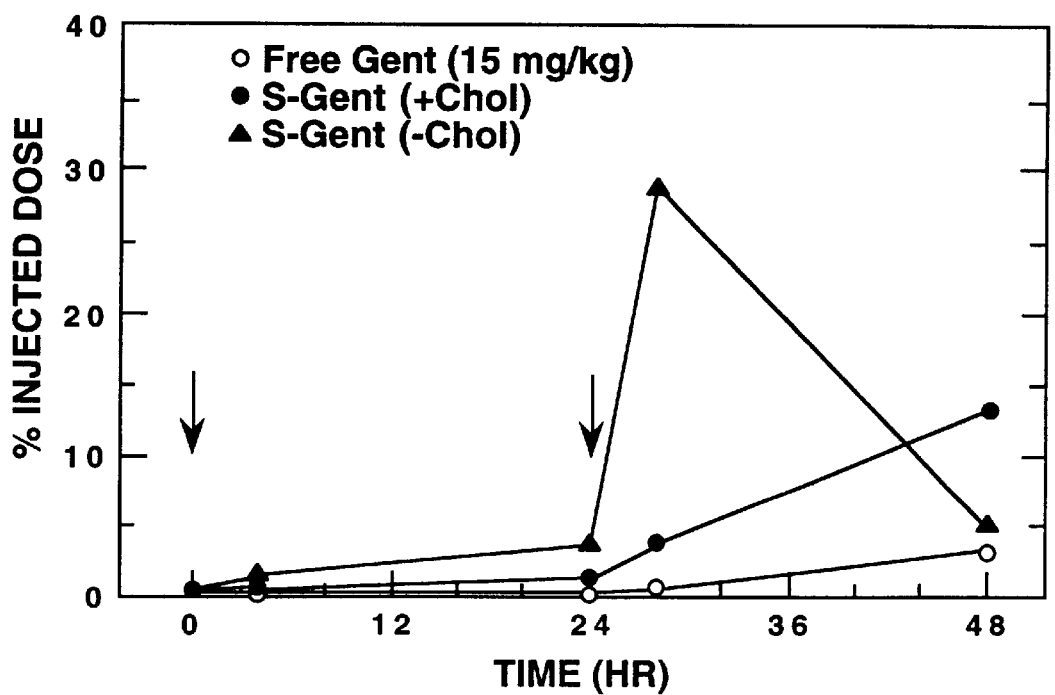
FIG. 18B is a plot similar to FIG. 18A, except that accumulation of gentamicin is expressed as percent of injected dose.

Similarly, it has been found that the percentage of cholesterol in the liposomes may be varied over a wide range without significant effect on observed blood/RES ratios. The studies presented in Example 7A, with reference to Table 6 therein, show virtually no change in blood/RES ratios in the range of cholesterol between 0–30 mole percent. On the other hand, cholesterol content may affect the kinetics of drug distribution to the infected tissue, as illustrated in FIGS. 18A and 18B.

It has also been found, in studies conducted in support of the invention, that blood/RES ratios are also relatively unaffected by the presence of charged lipid components, such as phosphatidylglycerol (PG). This can be seen from FIG. 7, which plots percent loss of encapsulated marker for PEG-PE liposomes containing either 4.7 mole percent PG (triangles) or 14 mole percent PG (circles). Virtually no difference in liposome retention in the bloodstream over a 24 hour period was observed. The option of including negative charge in the liposome without aggravating RES uptake provides a number of potential advantages. Liposomes suspensions which contain negative charge tend to be less sensitive to aggregation in high ionic strength buffers and hence physical stability is enhanced. Also, negative charge present in the liposome membrane can be used as a formulation tool to effectively bind high amounts of cationic drugs.

Figure 9:
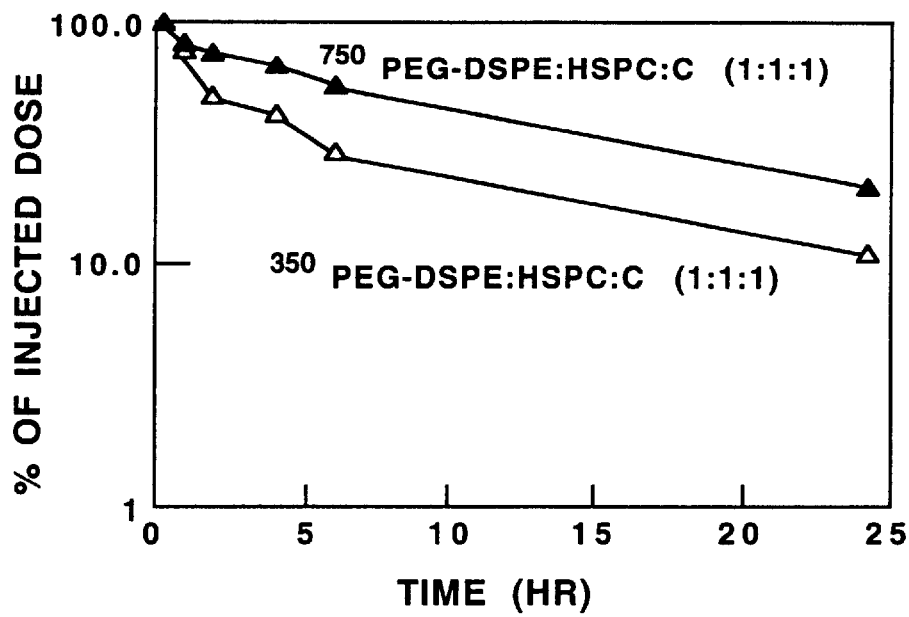
FIG. 9 is a plot similar to that of FIG. 7, showing the blood residence times of liposomes formulated with PEG having a molecular weight of 750 (solid triangles) and PEG having a molecular weight of 350 (open triangles)

The vesicle-forming lipid derivatized with a biocompatible hydrophilic polymer is also present in the liposomal composition. The amount of such derivatized hydrophilic polymer is preferably between about 1–20 mole percent, on the basis of moles of derivatized lipid as a percentage of total moles of vesicle-forming lipids. These preferred mole ratios are applicable particularly to lipids derivatized with PEG having molecular weights between about 1,000–5,000 daltons. It will be appreciated that a lower mole ratio, such as less than one mole percent, may be appropriate for a lipid derivative with a large molecular weight polymer, and that such a composition may be effective in achieving significantly enhanced liposome blood-circulation times when the hydrophilic polymer, e.g., PEG, has a relatively high molecular weight, e.g, greater than about 1,000–5,000 daltons. Conversely, a higher mole ratio will be effective for a lipid derivative having a low molecular weight polymer, such as PEG having a molecular weight of 350 daltons. Such a composition may also be effective in achieving significantly enhanced liposome blood-circulation times. This is illustrated in FIG. 9, which shows the blood-circulation time for liposomes composed of PEG having molecular weights of 350 and 750 were used at 33% molar ratios in liposome compositions. As seen, both compositions exhibited extended blood circulation times characteristic of the present invention. Specifically, such compositions extend blood circulation time as measured 24 hours after injection of the liposomes, at least several-fold over that achievable by liposomes lacking derivatized hydrophilic polymers.

As noted in Section I, the hydrophilic polymer in the derivatized lipid preferably has a molecular weight between about 200–20,000 daltons, and more preferably between about 300–5,000 daltons. Example 7B, which examines the effect of very short ethoxy ether moieties on blood/RES ratios indicates that polyether moieties of greater than about 5 carbon ethers are required to achieve significant enhancement of blood/RES ratios.

B. Preparing the Liposome Composition

The liposomes may be prepared by a variety of techniques, such as those detailed in Szoka et al, 1980. One method for preparing drug-containing liposomes is the reverse phase evaporation method described by Szoka et al. and in U.S. Pat. No. 4,235,871. The reverse phase evaporation vesicles (REVs) have typical average sizes between about 2–microns and are predominantly oligolamellar, that is, contain one or a few lipid bilayer shells. The method is detailed in Example 4A.

Multilamellar vesicles (MLVs) can be formed by simple lipid-film hydration techniques. In this procedure, a mixture of liposome-forming lipids of the type detailed above dissolved in a suitable organic solvent is evaporated in a vessel to form a thin film, which is then covered by an aqueous medium, as detailed in Example 4B. The lipid film hydrates to form MLVS, typically with sizes between about 0.1 to 10 microns.

In accordance with one important aspect of the invention, the liposomes are prepared to have substantially homogeneous sizes in a selected size range between about 0.07 and 0.2 microns. In particular, it has been discovered that liposomes in this size range are readily able to extravasate into infected regions, as discussed in Section III below, and at the same time, are capable of carrying a substantial drug load to an infected region and are capable of being filter sterilized. Although small unilamellar vesicles of less than $0.07\mu$ can easily extravasate into infection regions, they are severely restricted in drug-loading capacity. The upper end of this preferred size range, 0.1 microns, is not necessarily the largest size liposome capable of extravasation, rather it is approximately the upper limit of size of liposome which can be conventionally filter sterilized prior to administration. It can be appreciated that, allowing for adjustments in pharmaceutical formulation procedures, liposomal compositions above or below this size range may be effective in delivering drugs to an infected region.

One effective sizing method for REVs and MLVs involves extruding an aqueous suspension of the liposomes through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. This method of liposome sizing is used in preparing homogeneous-size REV and MLV compositions described in the examples below. A more recent method involves extrusion through an asymmetric ceramic filter. The method is detailed in U.S. Pat. No. 4,737,323 for Liposome Extrusion issued Apr. 12, 1988. Homogenization methods are also useful for down-sizing liposomes to sizes of 100 nm or less (Martin).

Other methods of reducing particle size include application of high pressures to the liposomes, as in a French Press, and homogenization of the liposomes. In experiments carried out in support of the present invention, high pressure extrusion was generally used to control particle size.

Homogenization techniques may be limited, to some degree, by the presence in the liposomal suspension of foam, production of which was found to occur to a greater extent in the gentamicin liposomal preparations than in the control liposomes. In experiments carried out in support of the present invention, it was found that the presence in the liposomal suspension of large amounts of foam resulted in a liposomal gentamicin composition characterized by particles having a minimum diameter of about 200 nm which were resistant to membrane extrusion.

C. Compound Loading

Incorporation of compound into liposomes can be achieved by one or more of a variety of active and passive methods. These methods and characteristics of exemplary compounds for use with these methods are described in detail in co-owned U.S. patent application Ser. No. 642,321, filed Jan. 15, 1991, which is incorporated herein by reference.

Passive loading by entrapment is employed for certain antimicrobial agents, particularly those which are therapeutically active at relatively low drug doses, and/or which are highly soluble in aqueous solutions. Here the drug is either dissolved in the aqueous phase used to hydrate the lipid or included with the lipids in liposome formation process, depending on the solubility of the compound.

According to one aspect of the invention, antibiotic agents, such as the aminoglycoside gentamicin, are loaded by passive hydration. In accordance with the invention it has been found that a hydration "cake" method, described in Example 12 is preferable for incorporation of relatively high concentrations of gentamicin into liposomes of the invention. In this method, a lipid "cake" is formed by lyophilization from a solution of lipids. The cake is then hydrated with an aqueous solution containing the drug to be incorporated into liposomes. Experiments carried out in support of the present invention in which the cake hydration method was tested using gentamicin sulfate concentrations from 20 to 100 mg/ml, and total lipid concentrations from 50 to 300 $\mu$mole/ml identified practical limits of $\leq$50 mg/ml for gentamicin and $\leq$150 $\mu$mole/ml for lipid. Above these concentrations, non-liposomal particles are formed. This method resulted in incorporation of 4–50% gentamicin sulfate, prior to removal of free drug (Example 12, Table 8).

Likewise, it was shown that hydration with aqueous gentamicin chloride of a lipid cake formed by lyophilization produces liposomal gentamicin compositions suitable for use in the invention. Liposomes formed by this process were characterized by apparent homogeneity of the initial dispersion and ease of extrusion. Incorporation of drug ranges from 6–24% prior to removal of free drug from the samples (Example 12, Table 11). Furthermore, studies in support of the present invention showed that substitution of cholesterol sulfate for cholesterol in the liposome lipid composition, when gentamicin chloride is used as loading drug, results in increased drug loading before removal of unincorporated drug (Cf. samples 42A, 42B, 42C in Table 11). In related experiments, it was found that omission of cholesterol from the lipid composition results in gentamicin sulfate loading of 70 $\mu$g/$\mu$mol lipid, with 83% entrapment after free drug removal.

Additional factors which might affect compound loading, including drug/lipid ratio and particle size have been investigated, in experiments carried out in support of the present invention. In general, increasing particle size or drug/lipid ratio during liposome formation results in an increase in final drug/lipid ratio (Table 10).

Figure 17:
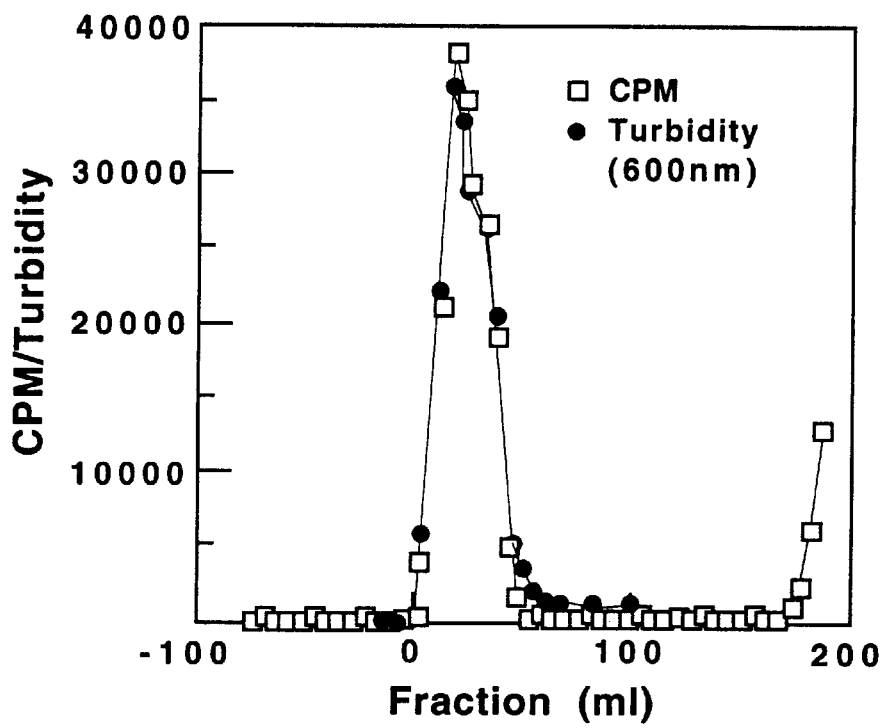
FIG. 17 shows a chromatographic profile of [$^{125}$I] gentamicin-containing liposomes eluting from a Sephadex G-50 size exclusion column, where radioactivity (open squares) and turbidity (light absorbance at 600 nm; diamonds) were monitored.

After liposome formation and sizing, free (unbound) drug is removed by ion exchange or gel exclusion chromatographic methods (described in Example 12C) or by dialysis or diafiltration. For gentamicin liposomal formulations, experiments in support of the present invention indicated that removal of free drug is most efficiently and completely carried out using column chromatography, such as on a Sephadex G-50 sizing column, followed by concentration. FIG. 17 shows a column profile of elution of [$^{125}$I] gentamicin-containing liposomes using this method. As is apparent from Tables 12 and 13, following removal of unentrapped drug, the ratio of bound gentamicin to lipid in the liposomal composition drops considerably, typically to about 20 $\mu$g/$\mu$mole for gentamicin sulfate (Table 12) and to about 50–70 $\mu$g/$\mu$mole for gentamicin chloride (Table 13). Percent incorporation of drug into liposomes following free drug removal ranges from 20–98% for gentamicin sulfate (Table 12) and from 40–85% for gentamicin chloride (Table 13).

Antibiotic liposomal compositions are stable to storage at refrigerated temperatures. Gentamicin sulfate containing liposomal compositions prepared as described above were stored at 8° C. and assayed for gentamicin content over the course of two weeks. As shown in Table 15, the drug to lipid ratio achieved after cleanup with G-50 Sephadex was essentially maintained over this period of time.

In summary, preferable conditions for entrapment of gentamicin into PEG-containing liposomes are as follows: Cakes containing 1000 $\mu$moles lipid are hydrated with 2.5 ml of gentamicin sulfate (200 mg/ml) in water by shaking for one hour. The suspension is diluted to 10 ml with isotonic saline, to a working concentration of 50 mg/ml gentamicin sulfate and 100 $\mu$moles lipid/ml. The dispersions are extruded to give a selected mean particle size which is preferably less than about 200 nm. Unentrapped drug is removed by gel chromatography, and the total volume reduced by centrifugation in a Centiprep-10 concentrator.

Where the antibiotic compound includes a peptide or protein drug, such as alpha interferon, the liposomes are preferably prepared by the reverse phase method, by a solvent injection system, such as described in U.S. Pat. No. 4,752,425, or by rehydrating a freeze dried mixture of the protein and a suspension of small unilamellar vesicles with water (Kirby). Both methods combine passive loading with relatively high encapsulation efficiency, e.g., up to 50% efficiency. Nonencapsulated material can be readily removed from the liposome suspension, e.g., by dialysis, diafiltration or exclusion chromatography.

In some cases, in order to entrap high concentrations of drugs in liposomes, it has been found to be useful to use active loading methods. One method for active loading of amphipathic drugs into liposomes is described in co-owned U.S. patent application Ser. No. 413,037, filed Sep. 28, 1988. In this method, liposomes are prepared in the presence of a relatively high concentration of ammonium ion sulfate. After sizing the liposomes to a desired size, the liposome suspension is treated to create an inside-to-outside ammonium ion gradient across the liposomal membranes. The gradient may be created by dialysis or diafiltration against a non-ammonium containing medium, such as an isotonic glucose medium, or by gel filtration, such as on a Sephadex G-50 column equilibrated with 0.15M NaCl or KCl effectively replacing ammonium sulfate in the exterior phase with sodium or potassium ions or a nonelectrolyte species. Alternatively, the liposome suspension may be diluted with a non-ammonium solution, thereby reducing the exterior-phase concentration of ammonium ions. The ammonium sulfate concentration inside the liposomes is preferably at least 10 times, and more preferably at least 100 to 1000 times that in the external liposome phase.

The ammonium sulfate gradient across the liposomes in turn creates a chemical gradient which permits capturing of unionized amines as they pass through the membrane, as ammonia is released across the liposome membrane, and the drugs are pronated and trapped in the internal aqueous phase of the liposome. To load liposomes with the selected drug a suspension of the liposomes, e.g., about 20–200 mg/ml lipid, is mixed with an aqueous solution of the drug, and the mixture is allowed to equilibrate over an period of time, e.g., several hours, at temperatures ranging from room temperature to 60° C.—depending on the phase transition temperature of the lipids used to form the liposome. In one typical method, a suspension of liposomes having a lipid concentration of 50 $\mu$moles/ml is mixed with an equal volume of amphipathic drug at a concentration of about 5–8 mg/ml. At the end of the incubation period, the suspension is treated to remove free (unbound) drug. One preferred method of drug removal for drugs is by passage over an ion exchange resin, such as Dowex 50 WX-4, which is capable of binding unencapsulated drug, but not liposomes containing the drug.

III. Liposome Localization in Infected Regions

A. Extended Bloodstream Halflife

One of the requirements for liposome localization in a target infected tissue, in accordance with the invention, is an extended liposome lifetime in the bloodstream following parenteral liposome administration. One measure of liposome lifetime in the bloodstream is the blood/RES ratio determined at a selected time after liposome administration, as discussed above. Blood/RES ratios for a variety of liposome compositions are given in Table 3 of Example 5. In the absence of PEG-derivatized lipids, blood/RES ratios were 0.03 or less. In the presence of PEG-derivatized lipids, the blood/RES ratio ranged from 0.2, for low-molecular weight PEG, to between 1.7–4 for several of the formulations, one of which lacks cholesterol, and three of which lack an added charged phospholipid (e.g., PG).

The data presented in Table 5 in Example 6 show blood/RES ratios (excluding two points with low percent recovery) between about 1.26 and 3.27, consistent with the data given in Table 3. As noted in Section II above, the blood lifetime values are substantially independent of degree of saturation of the liposome lipids, presence of cholesterol and presence of charged lipids.

The blood/RES values reported above can be compared with blood/RES values reported in co-owned U.S. Pat. No. 4,920,016, which used blood/RES measurement methods similar to those used in generating the data presented in Tables 3 and 5. The best 24-hour blood/RES ratios which were reported in the above-noted patent was 0.9, for a formulation composed of $GM_1$, saturated PC, and cholesterol. The next best formulations gave 24-hour blood/RES values of about 0.5. Thus, typical 24-hour blood/RES ratios obtained in a number of the current formulations were more than twice as high as the best formulations which have been reported to date. Further, ability to achieve high blood/RES with $GM_1$, or HPI lipids was dependent on the presence of predominantly saturated lipids and cholesterol in the liposomes.

Figure 7:
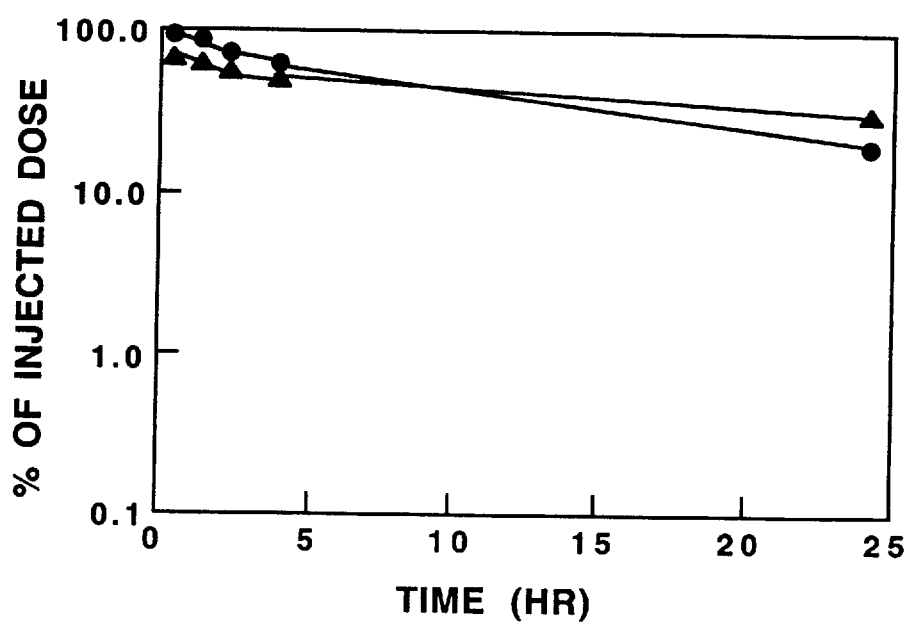
FIG. 7 is a plot of liposome residence times in the blood, expressed in terms of percent injected dose as a function of hours after IV injection, for PEG-PE liposomes containing 4.7 (triangles) or 14 (circles) mole percent of phosphatidylglycerol.
Figure 8A:
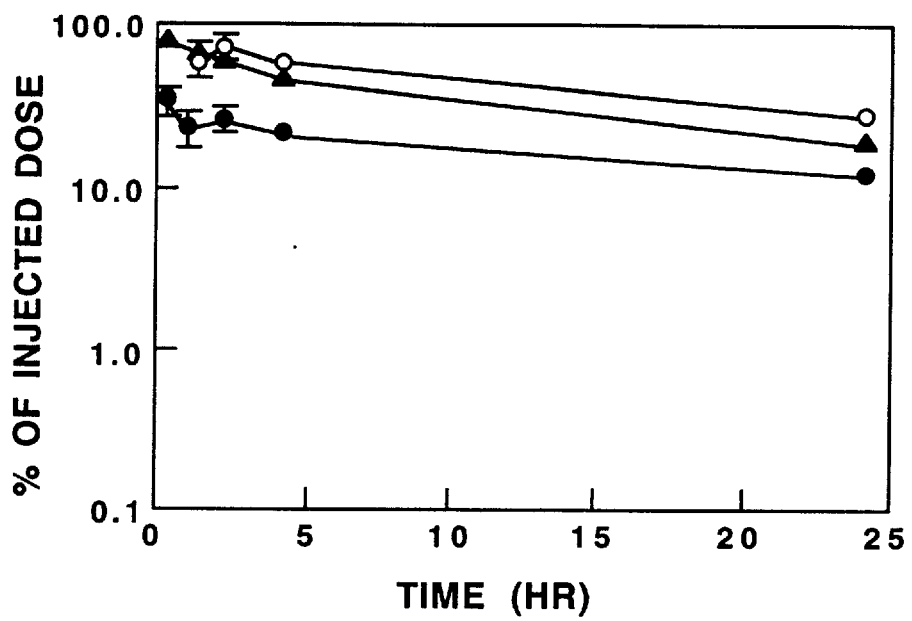
FIG. 8A is a plot similar to that of FIG. 7, showing blood residence times of liposomes composed of predominantly unsaturated phospholipid components.

Plasma pharmacokinetics of a liposomal marker in the bloodstream can provide another measure of the enhanced liposome lifetime which is achieved by the liposome formulations of the present invention. FIGS. 7 and 8A discussed above show the slow loss of liposomal marker from the bloodstream over a 24 hour period in typical PEG-liposome formulations, substantially independent of whether the marker is a lipid or an encapsulated water-soluble compound (FIG. 8A). In both plots, the amount of liposomal marker present 24 hours after liposome injection is greater than 10% of the originally injected material.

Figure 8B:
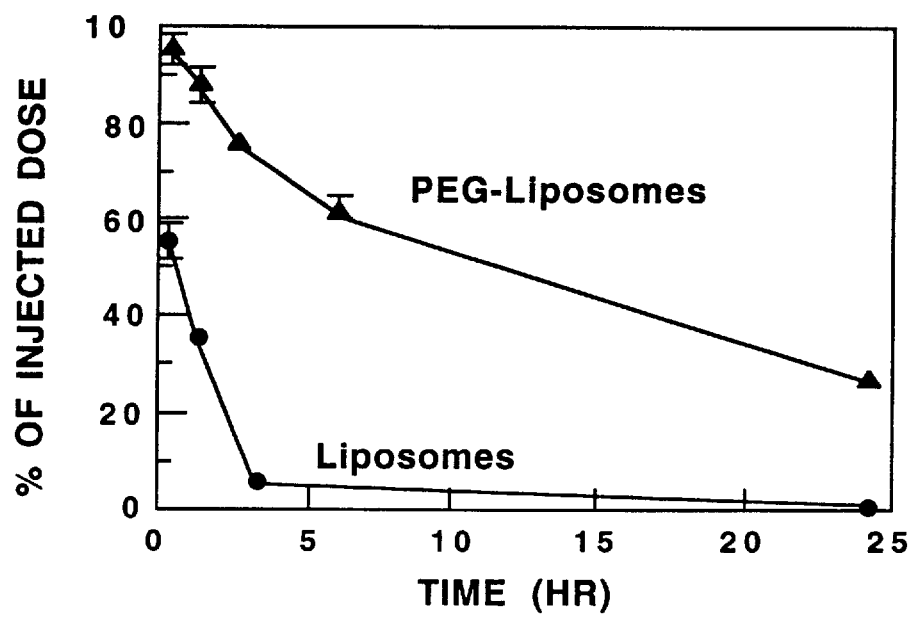
FIG. 8B is a plot similar to that of FIG. 7, showing the blood residence times of PEG-coated liposomes (solid triangles) and conventional, uncoated liposomes (solid circles)

FIG. 8B shows the kinetics of liposome loss from the bloodstream for a typical PEG-liposome formulation and the same liposomes in the absence of a PEG-derivatized lipid. After 24 hours, the percentage of PEG-liposomes remaining in the blood was greater than about 20%, whereas the conventional liposomes showed less than 5% retention in the blood after 3 hours, and virtually no detectable marker at 24 hours. FIG. 9 shows the kinetics of liposome loss from the bloodstream for low molecular weight PEG liposome formulations using DSPE derivatized to PEG having a molecular weight of 350 (350 PEG, open triangles) or 750 (750 PEG, closed triangles). These formulations showed blood retention times similar to those observed with liposomes formulated using higher molecular weight PEG (typically 1000–5000 daltons).

Similarly, liposomes containing PLA- or PGA-derivatized PE or PVA-derivatized DSPE show plasma kinetics which are superior to conventional liposomes consisting of PG, PC and cholesterol (FIGS. 10A and 10B), in that the liposomes containing the derivatized PE or DSPE are cleared from the bloodstream at a rate which is several-fold slower than the formulations without the derivatized PE or DSPE.

The results seen in FIGS. 7–10 are consistent with 24 hour blood liposome values measured for a variety of liposome formulations, and reported in Tables 3 and 5–7 in Example 5–8 below. As seen in Table 3 in Example 5, the percent dose remaining at 24 hours was less than 1% for conventional liposomes, versus at least 5% for the PEG-liposomes. In the best formulations, values between about 20–40% were obtained. Similarly in Table 5 from Example 6, liposome levels in the blood after 24 hours (again neglecting two entries with low recovery values) were between 12 and about 25 percent of total dose given. Similar results are reported in Tables 6 and 7 of Example 7.

For both blood/RES ratios, and liposome retention time in the bloodstream, the data obtained from a model animal system can be reasonably extrapolated to humans and veterinary animals of interest. This is because uptake of liposomes by the fixed macrophages of liver and spleen has been found to occur at similar rates in several mammalian species, including mouse, rat, monkey, and human (Gregoriadis, 1974; Jonah; Kimelberg, 1976; Juliano; Richardson; Lopez-Berestein). This result likely reflects the fact that the biochemical factors which appear to be most important in liposome uptake by the RES—including optimization by serum lipoproteins, size-dependent uptake effects, and cell shielding by surface moieties—are common features of all mammalian species which have been examined.

Comparison of PEG-containing liposomes of the invention with conventional liposome preparations reveals that a desirable feature of antimicrobial therapy—prolongation of blood levels of drug-carrying liposomes for two or more days in order to give increased and sustained accumulation in target sites—was not achieved by conventional liposomal preparations, but is achieved with the hydrophilic polymer-derivatized liposomal formulation of the invention, as exemplified by PEG-, PGA-, PLA-, and PVA-derivatized liposomal formulations (FIGS. 8B, 9, 10A and 10B).

B. Extravasation into Infected Tissues

Another required feature for high-activity liposome targeting to an infected region, in accordance with the invention, is liposome extravasation into the region through the endothelial cell barrier and underlying basement membrane separating a capillary from the tissue cells supplied by the capillary. Liposomes with sizes between about 0.07 and 0.2 microns exhibit this ability to extravasate into infected regions. Although liposomes with sizes of less than 0.07 microns would also be expected to extravasate, a limited drug-carrying capacity of these small liposomes render them less effective as drug carriers for the present system. Similarly, liposomal sizes greater than 0.2 microns may also extravasate to infected regions; however, as stated in Section II, such liposomes cannot easily be filter sterilized, following hydration, in conventional pharmaceutical production. For the purposes of the present invention, then, the optimal size range for liposomes would strike a balance between ability to extravasate, drug-carrying capacity, and feasibility of sterile filtration, that is, between 0.07 and 0.2 microns in diameter.

That liposome delivery to the infected region is required for selective drug targeting is demonstrated by experiments carried out in support of the present invention, in which approximately $10^5$ CFU of *Klebsiella pneumoniae* were administered to the left lungs of rats via intubation, as detailed in Example 11. Within 3–4 days, bacterial numbers in the left lung increased up to $2 \times 10^{10}$ and bacteria were present in the bloodstream. Severity of infection, assessed by bacterial number, was accompanied by a proportional increase in weight of the infected left lung from 0.5 g to up to 2 g and macroscopic evidence of infection. Pneumonic lesions were characterized by edema (fluid accumulation and weight gain), large numbers of Gram-negative bacilli, and a cellular infiltrate composed of polymorphonuclear leukocytes and macrophages. Although bacteria were also found in the right (uninfected) lung in numbers ranging from 10 to $10^9$ per lung, their presence was not associated with edematous mass increase or the histological markers described above.

Figure 11:
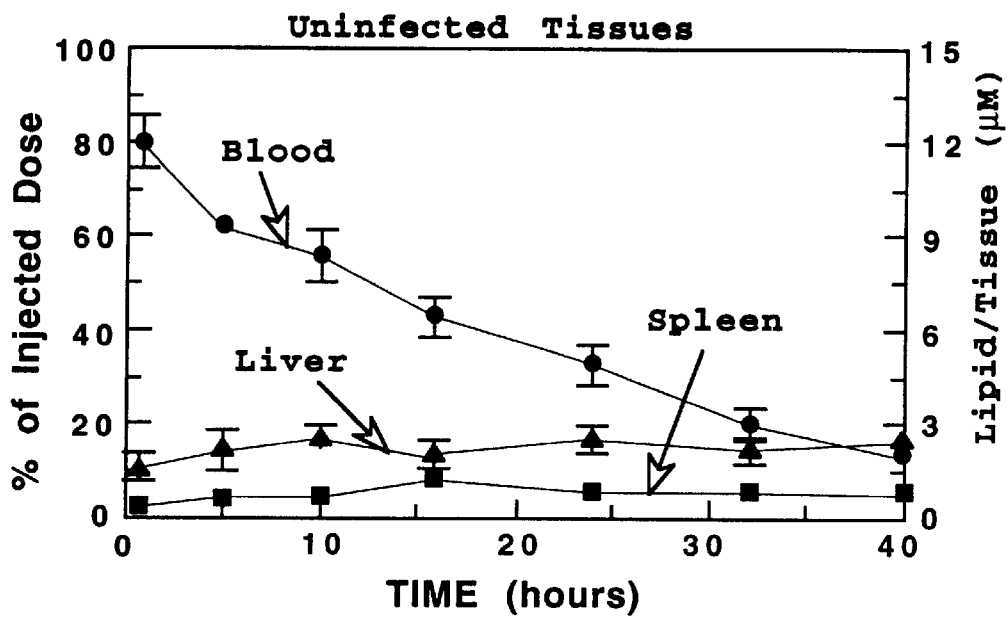
FIG. 11 shows a plot of the time course of distribution of PEG-containing liposomes in blood (solid circles), liver (solid triangles) and spleen (solid squares) in uninfected rats.

Three days following inoculation with bacteria, PEG-derivatized liposomes, having a composition ratio of PEG-DSPE:HSPC:CHO=0.15:1.85:1 and loaded with $^{67}$Ga as described in Example 4, were injected into the infected rats. Animals were sacrificed at various times following liposome injection, and uptake of liposomes by the lungs and other tissues assessed by measuring the amount of associated radioactivity by gamma scintigraphy. In uninfected animals, the PEG-containing liposomes elicited the usual reduced MPS uptake (liver and spleen) and remained in the blood for prolonged times, in agreement with earlier results (Woodle et al., 1990 and 1991; Papahadjopoulos et al., 1991). In uninfected animals, the prolonged blood circulation was not altered, as demonstrated by the plot shown in FIG. 11, in which it is apparent that liposome accumulation in the liver (solid triangles) and spleen (solid squares) are less than 20% and 10%, respectively, of the injected dose over the monitoring period (40 hours), and that these levels are well below the levels maintained in the blood during most of the monitoring period, and significantly, during the first 24 hours following injection.

Figure 12:
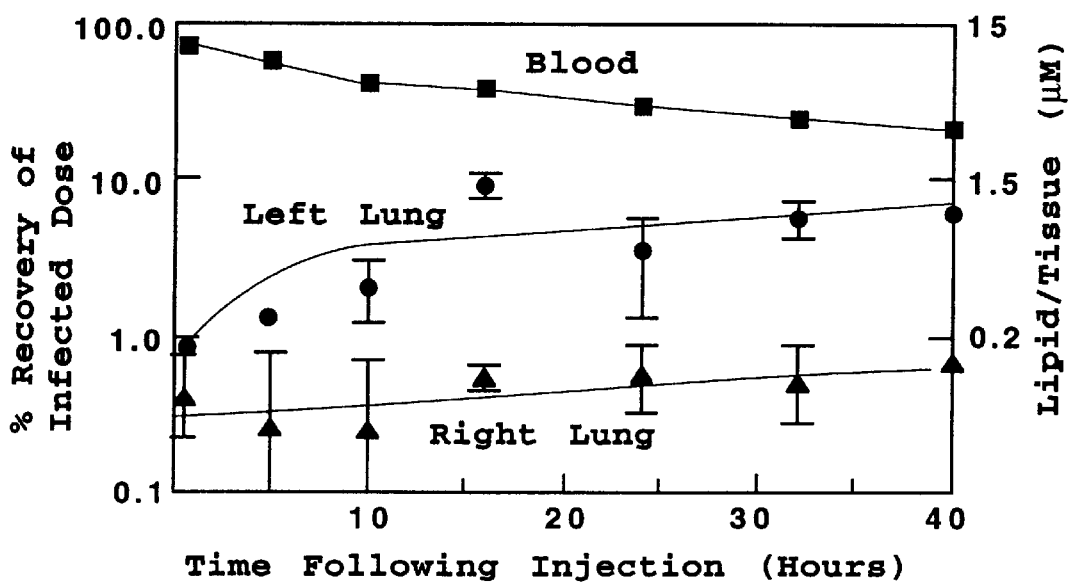
FIG. 12 shows a plot of the time course of accumulation of PEG-containing liposomes having mean diameters of 90 nm in uninfected right lungs (closed triangles), infected left lungs (closed circles) and blood (closed squares) of rats (n=4) infected locally in the left lung with $K.$ $pneumoniae;$
Figure 13:
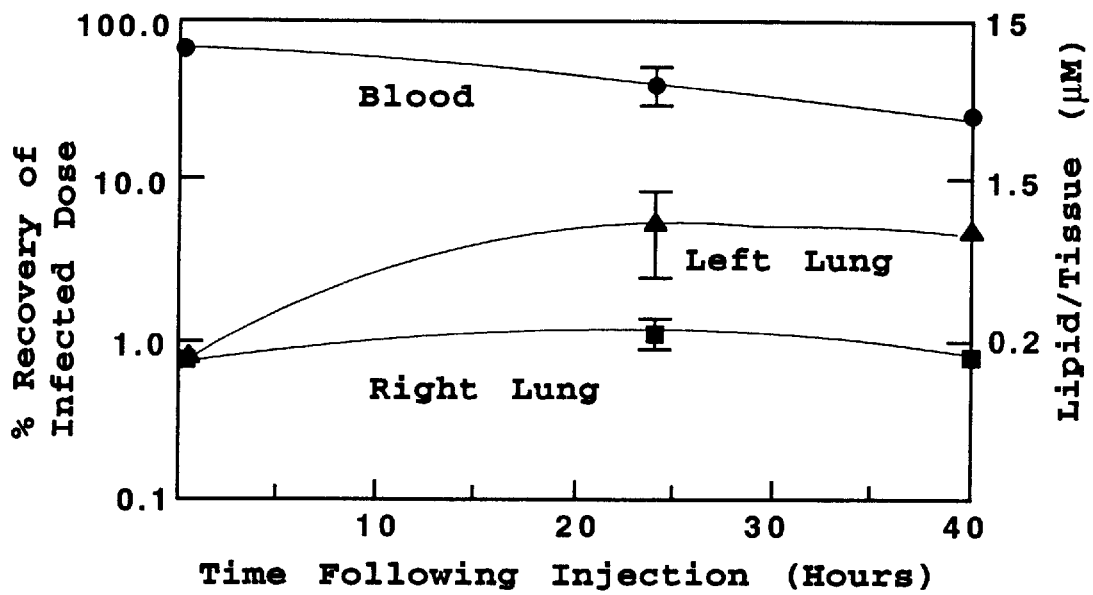
FIG. 13 shows a plot of recovery at various times (hours) after injection of PEG-containing liposomes having mean diameters of 150 nm from uninfected right lungs (open squares), infected left lungs (open triangles) and blood (open circles) of rats (n=4) infected locally in the left lung with $K.$ $pneumoniae;$

FIG. 12 shows the uptake kinetics of 90 nm $^{1900}$PEG-PE containing liposomes by the left (infected) and right (uninfected) lungs of rats over a 40 hour time period following injection of the liposomes, as detailed in Example 13. Similarly, FIG. 13 shows uptake kinetics of 150 nm liposomes. Blood levels of the liposomes are also plotted in the figures. Both 90 nm and 150 nm PEG-containing liposomes circulated in the bloodstream for prolonged periods, producing blood levels in excess of 20% of injected dose, 24 hours after injection, and approaching 10% of the injected dose, 40 hours following injection. In addition, both sizes of liposomes are selectively accumulated in infected lung tissue. Right lung levels in infected animals are typical of lung accumulation in uninfected animals. The left lung accumulation shows a maximum at 16 hours which is maintained for at least another 16 hours. After 48 hours, 6% of the injected dose of 90 nm liposomes was found in the infected lung, whereas only less than 0.5% of the injected dose was found in the uninfected lung (FIG. 12). Similar trends were observed for the 150 nm liposomes (FIG. 13).

Figure 14:
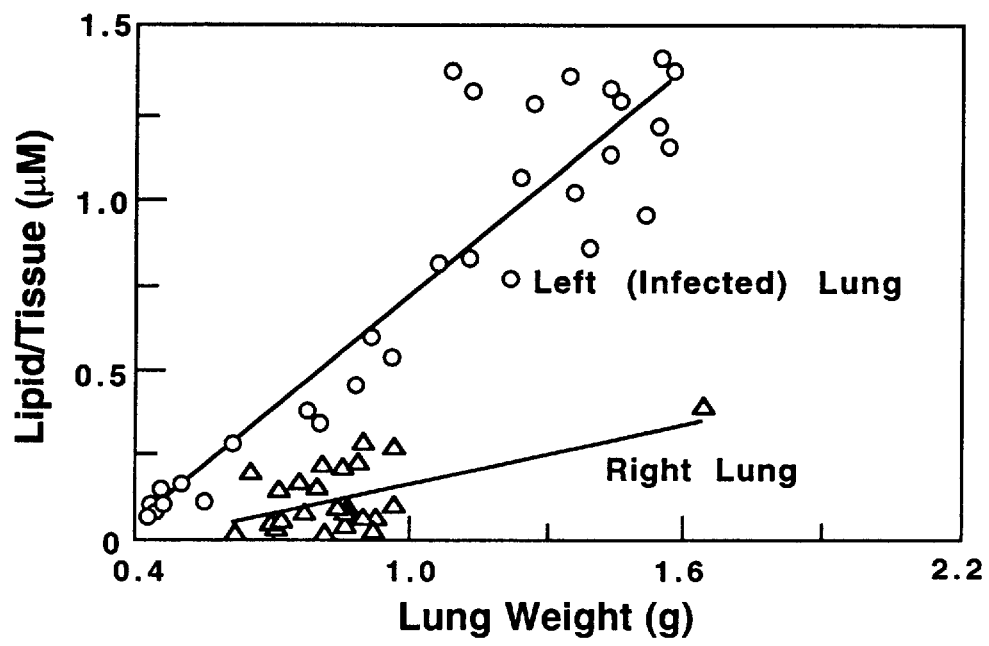
FIG. 14 shows a comparison of uptake of PEG-containing liposomes vs. lung weight in infected (left, circles) and noninfected (right, triangles) lungs.

A correlation between lung weight (an indicator of edema and severity of infection, as confirmed by histological examination) and liposomal uptake was also confirmed in the rat infection model described above. FIG. 14 shows a plot of lung weight vs. liposomal lipid accumulation per tissue volume at the 48 hour time point for left (infected) and right (uninfected) lung tissue in a large number of rats injected with $^{67}$Ga-labeled 90 nm liposomes. A comparison of accumulation in the infected left lung vs. accumulation in the uninfected right lung shows a correlation of liposomal uptake in the site of infection (left lung) with lung weight (FIG. 14; linear regression: r=0.92, p<0.01). Up to 9% of the liposome label was found to accumulate in the infected lung. In terms of lipid, the amount of accumulation varied from about 0.25 to 1.3 $\mu$M lipid/g lung (or about 0.1 to 1.4 $\mu$M lipid/lung). In contrast to the infected left lung, no correlation was observed between lung weight and liposome accumulation in uninfected right lungs (FIG. 14).

Figure 15A:
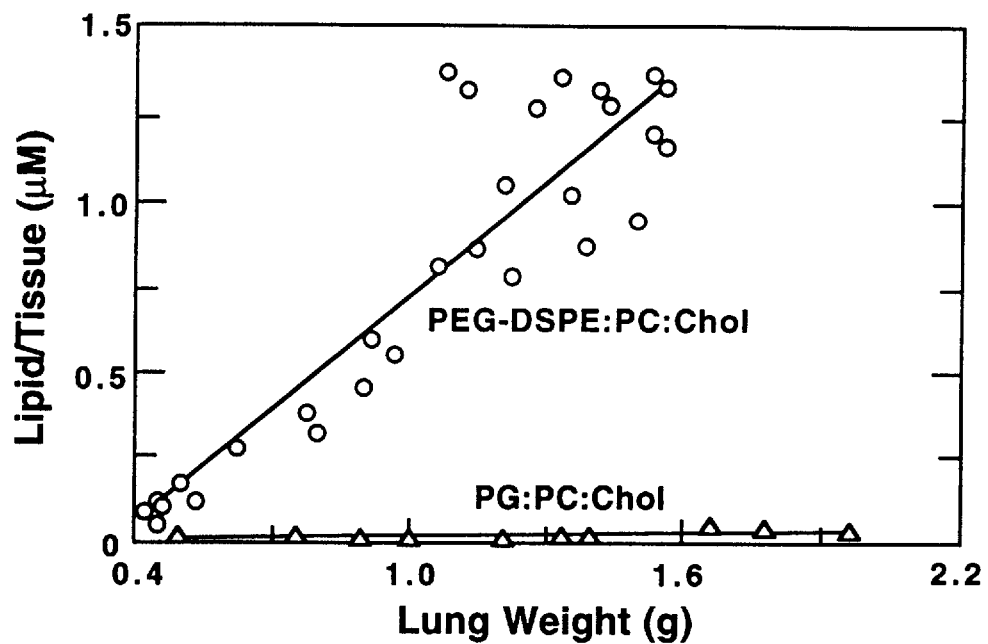
FIG. 15A shows the relationship between infected lung weight and uptake of $^{1900}$PEG-containing liposomes (circles) and uptake of control (PG:PC:chol; triangles) liposomes 48 hours after injection into rats, where uptake is expressed as $\mu$M liposomal lipid accumulation.
Figure 15B:
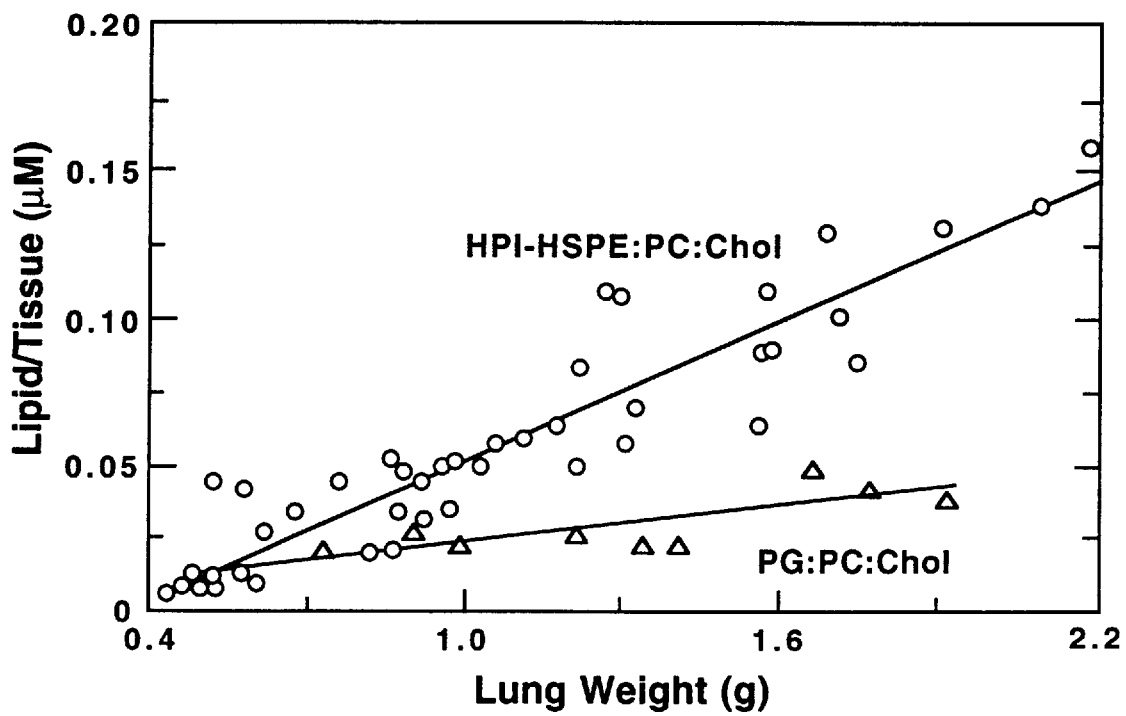
FIG. 15B shows the relationship between infected lung weight and uptake of HPI-containing liposomes (circles) and uptake of control (PG:PC:chol; triangles) liposomes 48 hours after injection into rats, where uptake is expressed as $\mu$M liposomal lipid accumulation.
Figure 16A:
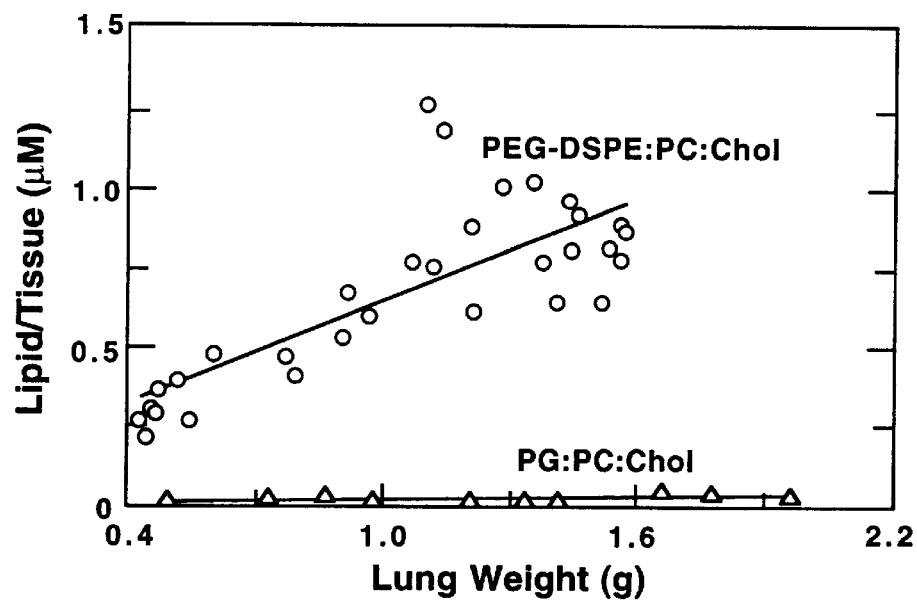
FIGS. 16A and 16B are plots of the data shown in FIGS. 15A and 15B respectively, where the uptake of liposomes is expressed as concentration of liposomal lipid per gram lung tissue.
Figure 16B:
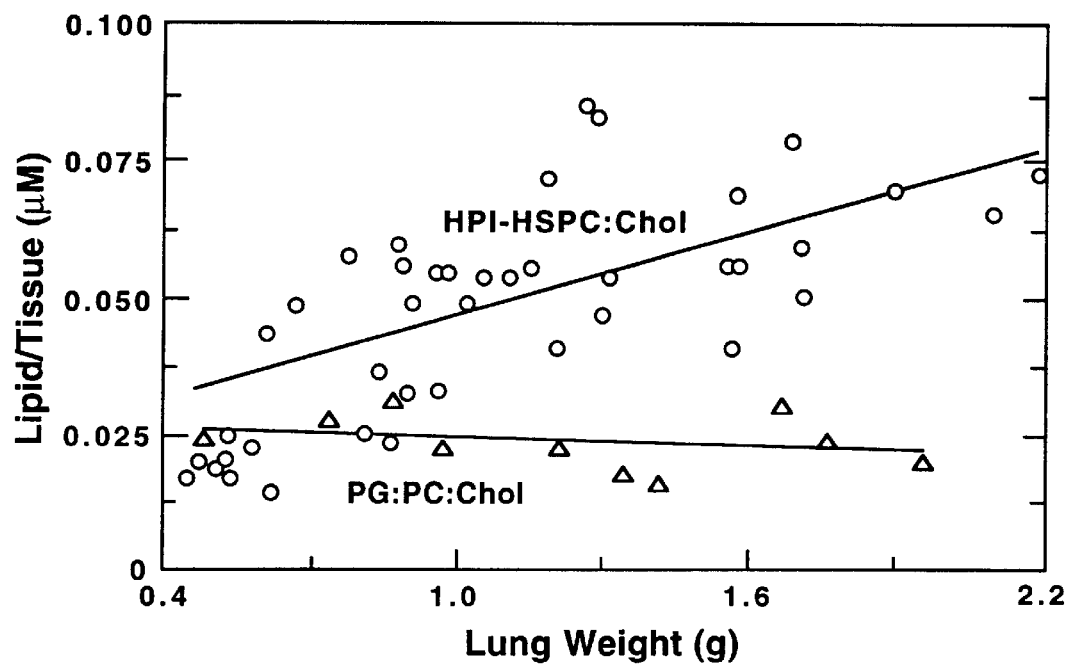

In accordance with the invention, it was found that PEG-DSPE-containing liposomes selectively accumulated in infected lungs, as compared to a conventional PG-PC-cholesterol liposome formulation. This selective accumulation by PEG-DPSE-containing liposomes is observed to be about 20-fold higher than is observed with the conventional (PG:PC:Chol) liposomes (FIG. 15A). In contrast, an HPI-containing liposomal formulation reported to produce an extended circulation time was examined for ability to selectively accumulate in infected lung tissue. As shown in FIG. 15B, such liposomes accumulated to a concentration only about 2–3 fold higher than that of conventional liposomes. In these studies it is also apparent that, in comparison to the HPI-containing liposomes, administration of PEG-DSPE-containing liposomes of the invention results in an approximately 10-fold higher concentration of lipid accumulation in the infected lung (FIGS. 15A and 15B, noting units on ordinate axes). Expression of these data as uptake per gram lung tissue, as shown in FIGS. 16A and 16B, permits assessment of whether the accumulation that occurs is simply a fixed concentration in the lung that increases due to the enlargement of the lung (edema) or whether a net increase accumulation per gram of lung tissue occurs. This analysis shows that the concentration of PEG-containing liposomes which accumulated per gram of lung tissue increased from roughly 0.25 to at least 0.75 $\mu$M/g, as severity of infection, as assessed by degree of edema, increased (FIG. 16A). In contrast, the liposomal formulation containing HPI rather than hydrophilic polymer derivatized lipids accumulated in infected tissue to a maximum average concentration of about 0.075 $\mu$M/g.

FIGS. 18A and 18B show the results of studies in which liposomal and non-liposomal gentamicin sulfate were administered separately to rats previously subjected to pulmonary infection by *K. pneumoniae*. Accumulation of gentamicin in the infected lung was measured, as described in Example 15. The dose of non-liposomal gentamicin administered (15 mg/kg) was approximately 8-fold higher than the dose of liposomal gentamicin administered (1.9 mg/kg). Nonetheless, as is apparent in FIG. 18A, accumulation of gentamicin in the lungs of animals given the liposomal formulations was generally equivalent or higher than accumulation of gentamicin in the lung of the animal given the higher dose of the non-liposomal formulation over most of the time period monitored. The same data, expressed as percentage of injected dosage, is shown in FIG. 18B, where it is apparent that the liposomal formulation delivers a higher percentage of the injected compound to the site of infection.

Therapeutic efficacy of liposomal compositions of the invention has been demonstrated, in experiments detailed in Example 16. Here, rats were infected in the left lung with *K. pneumoniae*, as described in Example 11. Twenty-four hours later, the rats were administered liposomal and non-liposomal compositions of gentamicin sulfate containing radiolabelled gentamicin as tracer. Samples were taken from the rat lungs at various times following injection, as shown, and cultured on bacterial plates using standard methods.

Figure 19:
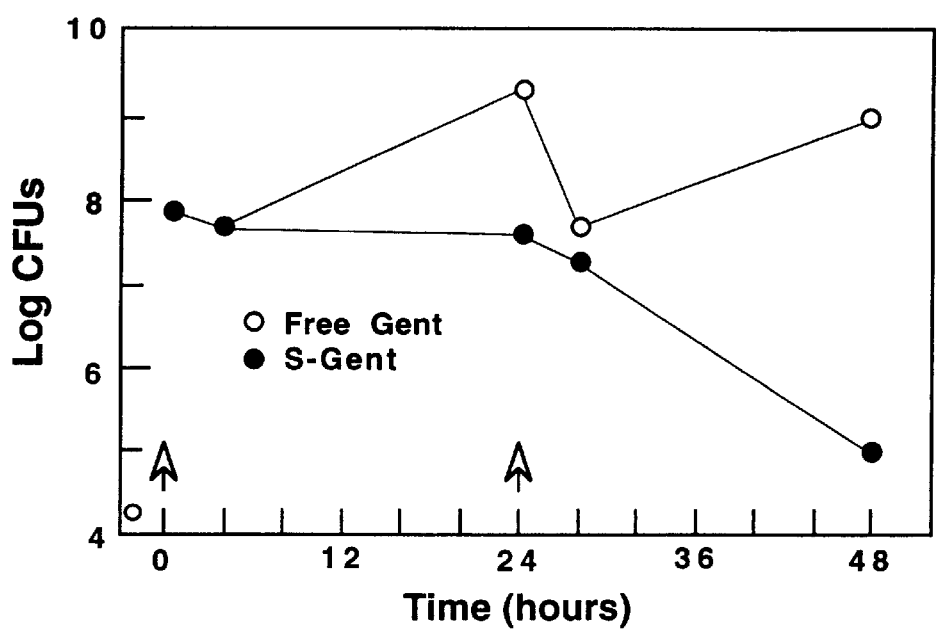
FIG. 19 is a plot of bacterial count (log CFU) in rat lungs infected with $K.$ $pneumoniae$ at time=0 and treated at time=24 hours with free gentamicin sulfate (15 mg/kg; open circles) or gentamicin sulfate-loaded PEG-containing liposomes (1.9 mg gentamicin/kg; solid circles).

Table 16 summarizes the results of the cultures, where data are expressed as log values of colony forming units (CFU) obtained from infected lung samples. Compared to administration of a comparable dose (1.9 mg/kg) of free gentamicin (far right column) administration of a liposomal composition (PEG:PC:CH) of gentamicin sulfate resulted in a 3-log reduction (1000-fold) in CFU (FIG. 19).

IV. Method of Localization of Liposomal Antimicrobial Formulations to Infected Regions As detailed above, liposomes of the invention are effective to localize and concentrate an entrapped antimicrobial or anti-infective drug specifically in an infected region. Liposome compositions preferably have a relatively high drug carrying capacity and minimal leakage of the entrapped drug during the time required for the liposomes to distribute to and enter the infected region (the first 24–48 hours following injection). The liposomes thus provide an effective method for concentrating the liposome-entrapped therapeutic compound in an infected region. In accordance with the invention, the antimicrobial compound is entrapped by such liposomes and the liposomal formulation is administered parenterally to a subject, preferably directly into the bloodstream. In the context of the present invention, an infected site or region is defined as one that is present anatomically at a site outside the bloodstream but which is adjacent to and accessible from a capillary bed. Infected regions which are most amenable to treatment by the method of the invention are characterized by an acute increase in permeability of the vasculature in the region of the infection, followed by migration of neutrophils out of the bloodstream into the infected region. In this case, for an IV injected liposome-antimicrobial composition to reach the infected site, it must leave the bloodstream and enter the infected region. In one preferred embodiment, the method of the invention is used to treat infection by localizing an antimicrobial agent selectively in the infected region. In studies carried out in support of the invention, gentamicin sulfate was loaded into PEG-containing liposomes of the invention, as detailed in Example 12. The antimicrobial agent forming a part of the liposomal composition of the invention is any compound, including the ones listed below, which can be stably entrapped by liposomes with a suitable loading factor, and which can be administered thereby to achieve a therapeutically effective concentration in the infected region.

The dose of injected liposomes required to produce a therapeutically effective concentration of agent at the site of infection can be closely approximated by measuring the percent accumulation of such liposomes in the relevant infected region in an appropriate animal model, as described above, the amount of drug loaded in the liposomal composition, and the minimal concentration of compound effective to inhibit or eradicate the infective agent of interest (Minimal Inhibitory Concentration, MIC). For example, in the case of gentamicin treatment of a Klebsiella infection, illustrated above, an MIC of gentamicin of about 1 $\mu$g/ml would be required at the lung site for of a treatment moderately infected rat lung. The dose of liposomes required to provide such a concentration to the lung can be calculated based on the known amount of entrapped drug per mass of liposomal lipid and the aforementioned liposome/drug distribution studies. Based on empirical as well as published data for standard antibiotic treatments, similar calculations can be made using published reference standard dosages for a variety of antimicrobial therapeutic compounds (Gilman).

General classes of antimicrobial agents which are used to treat internal microbial infections include antibacterial, antiviral, and antifungal agents. In addition, it is contemplated that the method of the invention can be used in the delivery of antiparasitic compounds useful in the treatment of certain protozoal and helminthic infections, when such infections are accompanied by increased capillary permeability in the infected region.

Antibacterial agents that can be used in the method of the invention include penicillin antibiotics, cephalosporin antibiotics, aminoglycoside antibiotics, tetracycline antibiotics, sulfonamide antibiotics, sulfone antibiotics, macrolide antibiotics, quinolone antibiotics, imipenem, isoniazid, ethambutol, aztreonam, chloramphenicol, erythromycin, clindamycin, spectinomycin, vancomycin, rifampin, clofazimine, bacitracin, methenamine, and nitrofurantoin. Antiviral agents include nucleoside analogs (zidovudine, acyclovir, gangcyclovir, vidarabine, idoxuridine, trifluridine, ribavirin), foscarnet, amantadine, and rimantadine. Also the liposomes may contain antimicrobial-therapeutic or immunomodulatory peptides and protein drugs, such as the alpha-interferons useful as adjunct antiviral therapy. Such agents may be present in the liposomes alone or in combination with other agents. Antifungal agents include amphotericin B, flucytosine, imidazoles and triazoles, and griseofulvin. Liposomal formulations containing appropriate combinations of such antimicrobial agents are also contemplated, in order to treat infections in which combination therapy is commonly prescribed.

Although reduced toxicity may contribute to the increased efficacy of the treatment method of the invention, selective localization of the drug by liposomal extravasation is also important for improved drug efficacy. Thus, by allowing both higher levels of drug to be administered, due to reduced drug toxicity in liposomes, and selective liposome localization in the intercellular fluid of the infected region, the drug delivery and treatment method of the invention provides better efficacy.

It will be appreciated that the ability to localize a compound selectively in an infected, by liposome extravasation, can also be exploited for non-invasive diagnosis and localization of infective agents. Here a microbe binding agent, typically a labeled antibody, is entrapped in liposomes, which are then administered IV to the subject being examined. After a selected period, typically 24–48 hours, the subject is then monitored, for example by gamma scintillation radiography in the case of a radiolabeled antibody, or by nuclear magnetic resonance (NMR) in the case of the paramagnetic agent, to detect regions of local uptake of the imaging agent.

V. Method of Treatment of Infected Regions

In accordance with the present invention, liposomes containing a derivatized biocompatible hydrophilic polymers effective to prolong blood circulation time are used to entrap therapeutic agents appropriate to treat a variety of localized infections or systemic infections having localized foci within the body. As described above, infected regions or sites which are amenable to treatment by the compositions of the invention are preferably adjacent to or accessible to capillary blood flow and at which increased capillary permeability occurs in response to infection. Appropriate therapeutic agents for liposomal entrapment and use against a variety of diseases can be determined with reference to one or more standard medical texts, such as Gilman.

Summarized here are several conditions which are exemplary of the types infections treatable by the method and liposomal compositions of the invention. It is understood that such conditions are presented as examples only, and that it is not intended that the usefulness of the method and composition of the invention be limited to such examples. It can appreciated that, generally, the treatment method of the invention is generally effective to treat infections of microbial origin, including viral, fungal, and bacterial infections, as well as infections of parasitic or helminthic origin.

Pulmonary infections have a number of etiologies and presentations. Aminoglycoside antibiotics are effective therapeutics against many of the virulent, gram-negative strains of bacteria that are causative agents in pneumonia; however, due to their toxicity, the use of such agents is suggested only in the case of life threatening infections, such as those due to *Pseudomonas aerupinosa*, Enterobacter, Klebsiella, Serratia, and other organisms which are found resistant to less toxic agents. Treatment of a Klebsiella infection of the lung is accomplished, using the treatment method and composition of the present invention, by administering to the patient a dose of liposomal formulation of an aminoglycoside, such as gentamicin. Such a formulation is administered in a dosage effective to produce a concentration of aminoglycoside effective to inhibit or reduce growth of the microorganism. In practice, a concentration of gentamicin in the lung of about 1 $\mu$g/ml is sufficient to produce a therapeutic effect. Similarly, pulmonary infections, and particularly lung abscesses, caused by the gram-negative bacterium Bacteroides can be effectively treated by administering a liposomal composition containing clindamicin or a cephalosporin or penicillin. Bacteroides anerobic infections involving other regions of the body, such as the bowel, pelvis or brain, are also amenable to such treatments, alone or in combination with other antimicrobial agents, including chloramphenicol and metronidazole.

As described earlier, the cells of the liver and spleen which normally (in the absence of infection) accumulate liposomes are the fixed macrophages which constitute part of the lymphoreticular, or RES, system. Accumulation of liposomes in these cells would not necessarily predict delivery of drug to adjacent tissue cells, such as hepatocytes of the liver parenchyma. On the other hand, such cells may be localized sites of certain infections, such as viral hepatitis. In the presence of such an infection, it is anticipated that hepatocytes would selectively accumulate liposomal drug compositions of the invention. Liposome entrapped DNA polymerase inhibitors, such as zidovudine, may be useful in the treatment of such infections.

The central nervous system, including the brain, spinal cord and meninges are also susceptible to infection by a number of causative agents. Although drug passage from the blood to such central nervous tissues is generally impeded by the "blood brain barrier", this barrier is known to break down considerably during meningeal infections, rendering such sites of infection more accessible to liposomal preparations of the invention. Hence, it is anticipated that a number of severe infections of the central nervous system are amenable to treatment by liposome entrapped antimicrobial compositions. Examples of such infections and liposome-entrapped drugs suitable for treatment include Cryptococcus treatment by amphotericin or fluconazole, Pneumococcus, Pseudomonas, Listeria and Meningococcus by penicillins, erythromycin, gentamicin or cephalosporins. In addition, bacterial meningitis due to *Hemophilus influenzae* or *Streptococcus pneumoniae* is treatable in some cases with penicillins or cephalosporins; however, particularly in patients exhibiting penicillin allergies, chloramphenicol remains a drug of choice for treatment of such infections, even in the face of its serious toxic side effects, including blood dyscrasias. Liposomal entrapment of chloramphenicol is anticipated to decrease the dose of compound to which uninfected, drug-sensitive tissues, including the bone marrow, are exposed.

Although many skin infections respond to topical treatment certain chronic infections of the dermis or epidermis may require systemic drug treatment for effective therapeutic results. One such dermal infection is caused by herpes virus. Treatment with liposome-entrapped acyclovir is appropriate for such an infection.

Aspergillus is a fungus which has been implicated as an infective agent in practically every organ of the body. It is commonly found as the causative agent in pervasive lung infections, particularly in immunocompromised patients. The treatment of choice for this type of infection is amphotericin B. In practicing, the method of the invention, liposome encapsulated amphotericin B is administered to a patient, at a dose effective to produce a concentration in the infected tissue of about 2 $\mu$g/ml.

A number of other sites in the body are particularly amenable to the treatment method of the invention, including those infections secondary to implantation of a prosthesis or medical device such as a heart valve or indwelling catheter. Such infections are characterized by the presence of a biofilm which renders them relatively resistant to standard doses of antibiotic agents. A region which is commonly infected as a result of the presence of an indwelling catheter is the prostate, where infection by Pseudomonas can be particularly severe. In such cases, treatment with high concentrations of penicillin or cephalosporin antibiotics is desirable.

Similarly, endocarditis may occur secondary to implantation of a heart valve. Staphylococcus is a common causative agent in such infections. The treatment method of the invention is used to deliver sufficiently high concentrations of vancomycin to the endocardium, to eradicate such an infection. When given in non-liposomal form, vancomycin is associated with several potentially debilitating toxicities which limit its use in effective concentrations.

Similarly, vancomycin is useful in the treatment of staphyllococcal osteomyelitis, which is commonly found as a complication of bone marrow transplant or joint replacement surgery. Cephalosporins and penicillins are also effective against certain forms of osteomyelitis, and liposomal formulations of these compounds are contemplated to be useful in the treatment of this condition.

The following examples illustrate methods of preparing liposomal formulations having enhanced circulation times which selectively accumulate in infected tissue and methods of administering such liposomal formulations in animal models of infection. The examples are intended to illustrate specific liposome compositions and methods of the invention, but are in no way intended to limit the scope thereof.

Materials

Cholesterol (Chol) was obtained from Sigma (St. Louis, Mo.). Sphingomyelin (SM), egg phosphatidylcholine (lecithin or PC), partially hydrogenated PC having the composition IV40, IV30, IV20, IV10, and IV1, phosphatidylglycerol (PG), phosphatidylethanolamine (PE), dipalmitoyl-phosphatidyl glycerol (DPPG), dipalmitoyl PC (DPPC), dioleyl PC (DOPC) and distearoyl PC (DSPC) were obtained from Avanti Polar Lipids (Birmingham, Ala.) or Austin Chemical Company (Chicago, Ill.). Distearyl phosphatidyl ethanolamine was obtained from Calbiochem (La Jolla, Calif.).

[$^{125}$I]-tyraminyl-inulin was made according to published procedures. $^{67}$Gallium-citrate was supplied by NEN Neoscan (Boston, Mass.). [$^{125}$I]gentamicin was from NEN (Cambridge, Mass.). Doxorubicin HCl and Epirubicin HCL were obtained from Adria Laboratories (Columbus. Ohio) or Farmitalia Carlo Erba (Milan, Italy).

Polyvinyl alcohol (PVA), glycolic acid, and lactic acid were from Aldrich (St. Louis, Mo.). Polylactic acid was supplied by ICN (Cleveland, Ohio).

EXAMPLE 1

Preparation of PEG-PE Linked by Cyanuric Chloride

A. Preparation of activated PEG 2-0-Methoxypolyethyleneglycol1900-4,6-dichloro-1,3,5 triazine previously called activated PEG was prepared as described in *J. Biol. Chem.*, 252:3582 (1977) with the following modifications.

Cyanuric chloride (5.5 g; 0.03 mol) was dissolved in 400 ml of anhydrous benzene containing 10 g of anhydrous sodium carbonate, and PEG-1900 (19 g; 0.01 mol) was added and the mixture was stirred overnight at room temperature. The solution was filtered, and 600 ml of petroleum ether (boiling range, 35–600) was added slowly with stirring. The finely divided precipitate was collected on a filter and redissolved in 400 ml of benzene. The precipitation and filtration process was repeated several times until the petroleum ether was free of residual cyanuric chloride as determined by high pressure liquid chromatography on a column (250×3.2 mm) of 5-m "LiChrosorb" (E. Merck), developed with hexane, and detected with an ultraviolet detector. Titration of activated PEG-1900 with silver nitrate after overnight hydrolysis in aqueous buffer at pH 10.0, room temperature, gave a value of 1.7 mol of chloride liberated/mol of PEG.

TLC analysis of the product was carried out on TLC reversed-phase plates obtained from Baker using methanol/water, 4:1; v/v, as developer and exposure to iodine vapor for visualization. Under these conditions, the starting methoxy polyglycol 1900 appeared at $R_f$=0.54 to 0.60. The activated PEG appeared at $R_f$=0.41. Unreacted cyanuric chloride appeared at $R_f$=0.88 and was removed.

The activated PEG was analyzed for nitrogen and an appropriate correction was applied in selecting the quantity of reactant to use in further synthetic steps. Thus, when the product contained only 20% of the theoretical amount of nitrogen, the quantity of material used in the next synthetic step was increased by 100/20, or 5-fold. When the product contained 50% of the theoretical amount of nitrogen, only 100/50 or a 2-fold increase was needed.

B. Preparation of N-(4-Chloro-polyethyleneglycol 1900)-1, 3,5-triazinyl egg phosphatidylethanolamine In a screw-capped test tube, 0.74 ml of a 100 mg/ml (0.100 mmole) stock solution of egg phosphatidylethanolamine in chloroform was evaporated to dryness under a stream of nitrogen and was added to the residue of the activated PEG described in section A, in the amount to provide 205 mg (0.100 mmole). To this mixture, 5 ml anhydrous dimethyl formamide was added. 27 microliters (0.200 mmole) triethylamine was added to the mixture, and the air was displaced with nitrogen gas. The mixture was heated overnight in a sand bath maintained at 110° C.

The mixture was then evaporated to dryness under vacuum and a pasty mass of crystalline solid was obtained. This solid was dissolved in 5 ml of a mixture of 4 volumes of acetone and 1 volume of acetic acid. The resulting mixture was placed at the top of a 21 mm×240 mm chromatographic absorption column packed with silica gel (Merck Kieselgel 60, 70–230 mesh) which had first been moistened with a solvent composed of acetone acetic acid, 80/20; v/v.

The column chromatography was developed with the same solvent mixture, and separate 20 to 50 ml aliquots of effluent were collected. Each portion of effluent was assayed by TLC on silica gel coated plates, using 2-butanone/acetic acid/water; 40/25/5; v/v/v as developer and iodine vapor exposure for visualization. Fractions containing only material of $R_f$=about 0.79 were combined and evaporated to dryness under vacuum. Drying to constant weight under high vacuum afforded 86 mg (31.2 micromoles) of nearly colorless solid N-(4-chloro-polyglycol 1900)-1,3,5-triazinyl egg phosphatidylethanolamine containing phosphorous.

The solid compound was taken up in 24 ml of ethanol/chloroform; 50/50 chloroform and centrifuged to remove insoluble material. Evaporation of the clarified solution to dryness under vacuum afforded 21 mg (7.62 micromoles) of colorless solid.

EXAMPLE 2

Preparation of Carbamate and Amide Linked Hydrophilic Polymers with PE

A. Preparation of the imidazole carbamate of polyethylene glycol methyl ether 1900.

9.5 grams (5 mmoles) of polyethylene glycol methyl ether 1900 obtained from Aldrich Chemical Co. was dissolved in 45 ml benzene which has been dried over molecular sieves. 0.89 grams (5.5 mmoles) of pure carbonyl diimidazole was added. The purity was checked by an infra-red spectrum. The air in the reaction vessel was displaced with nitrogen. Vessel was enclosed and heated in a sand bath at 75° C. for 16 hours.

The reaction mixture was cooled and the clear solution formed at room temperature. The solution was diluted to 50.0 ml with dry benzene and stored in the refrigerator as a 100 micromole/ml stock solution of the imidazole carbamate of PEG ether 1900.

B. Preparation of the phosphatidylethanolamine carbamate of polyethylene glycol methyl ether 1900

10.0 ml (1 mmol) of the 100 mmol/ml stock solution of the imidazole carbamate of polyethylene glycol methyl ether 1900 was pipetted into a 10 ml pear-shaped flask. The solvent was removed under vacuum. 3.7 ml of a 100 mg/ml solution of egg phosphatidyl ethanolamine in chloroform (0.5 mmol) was added. The solvent was evaporated under vacuum. 2 ml of 1,1,2,2-tetrachloroethylene and 139 microliters (1.0 mmol) of triethylamine VI was added. The vessel was closed and heated in a sand bath maintained at 95° C. for 6 hours. At this time, thin-layer chromatography was performed with fractions of the above mixture to determine an extent of conjugation on SiO2 coated TLC plates, using butanone/acetic acid/water; 40/5/5; v/v/v; was performed as developer. Iodine vapor visualization revealed that most of the free phosphatidyl ethanolamine of Rf=0.68, had reacted, and was replaced by a phosphorous-containing lipid at $R_f$=0.78 to 0.80.

The solvent from the remaining reaction mixture was evaporated under vacuum. The residue was taken up in 10 ml methylene chloride and placed at the top of a 21 mm×270 mm chromatographic absorption column packed with Merck Kieselgel 60 (70–230 mesh silica gel), which has been first rinsed with methylene chloride. The mixture was passed through the column, in sequence, using the following solvents.

TABLE 1

| ml | Volume % of Methylene Chloride | Volume % Methylene with 2% Acetic Acid |
|---|---|---|
| 100 | 100% | 0% |
| 200 | 95% | 5% |
| 200 | 90% | 10% |
| 200 | 85% | 15% |
| 200 | 60% | 40% |

50 ml portions of effluent were collected and each portion was assayed by TLC on SiO2—coated plates, using I2 vapor absorption for visualization after development with chloroform/methanol/water/concentrated ammonium hydroxide; 130/70/8/0.5%; v/v/v/v. Most of the phosphates were found in fractions 11, 12, 13 and 14.

These fractions were combined, evaporated to dryness under vacuum and dried in high vacuum to constant weight. They yielded 669 mg of colorless wax of phosphatidyl ethanolamine carbamate of polyethylene glycol methyl ether. This represented 263 micromoles and a yield of 52.6% based on the phosphatidyl ethanolamine.

An NMR spectrum of the product dissolved in deuterochloroform showed peaks corresponding to the spectrum for egg PE, together with a strong singlet due to the methylene groups of the ethylene oxide chain at Delta=3.4 ppm. The ratio of methylene protons from the ethylene oxide to the terminal methyl protons of the PE acyl groups was large enough to confirm a molecular weight of about 2000 for the polyethylene oxide portion of the molecule of the desired product polyethylene glycol conjugated phosphatidyethanolamine carbamate, M.W. 2,654.

C. Preparation of polylactic acid amide of phosphatidylethanolamine 200 mg (0.1 mmoles) poly (lactic acid), mol. wt.=2,000 (ICN, Cleveland, Ohio) was dissolved in 2.0 ml dimethyl sulfoxide by heating while stirring to dissolve the material completely. Then the solution was cooled immediately to 65° C. and poured onto a mixture of 75 mg (0.1 mmoles) of distearylphosphatidyl-ethanolamine (Cal. Biochem, La Jolla) and 41 mg (0.2 mmoles) dicyclohexyl-carbodiimide. Then 28 ml (0.2 mmoles) of triethylamine was added, the air swept out of the tube with nitrogen gas, the tube capped, and heated at 65° C. for 48 hours.

After this time, the tube was cooled to room temperature, and 6 ml of chloroform added. The chloroform solution was washed with three successive 6 ml volumes of water, centrifuged after each wash, and the phases separated with a Pasteur pipette. The remaining chloroform phase was filtered with suction to remove suspended distearolyphosphatidyl ethanolamine. The filtrate was dried under vacuum to obtain 212 mg of semi-crystalline solid.

This solid was dissolved in 15 ml of a mixture of 4 volumes ethanol with 1 volume water and passed through a 50 mm deep and 21 mm diameter bed of $H^+$ Dowex 50 cation exchange resin, and washed with 100 ml of the same solvent. The filtrate was evaporated to dryness to obtain 131 mg colorless wax.

291 mg of such wax was dissolved in 2.5 ml chloroform and transferred to the top of a 21 mm×280 mm column of silica gel wetted with chloroform. The chromatogram was developed by passing through the column, in sequence, 100 ml each of:

100% chloroform, 0% (1% $NH_4OH$ in methanol);
90% chloroform, 10% (1% $NH_4OH$ in methanol);
85% chloroform, 15% (1% $NH_4OH$ in methanol);
80% chloroform, 20% (1% $NH_4OH$ in methanol);
70% chloroform, 30% (1% $NH_4OH$ in methanol).

Individual 25 ml portions of effluent were saved and assayed by TLC on $SFO_2$-coated plates, using $CHCl_3$, $CH_3OH$, $H_2O$, con. $NH_4OH$, 130, 70, 8, 0.5 v/v as developer and $I_2$ vapor absorption for visualization.

The 275–325 ml portions of column effluent contained a single material, $PO_4+$, of $R_f$=0.89. When combined and evaporated to dryness, these afforded 319 mg colorless wax. Phosphate analysis of the substance confirmed a molecular weight of about 115,000. This material was used to produce polylactic acid-PE containing liposomes used in experiments summarized in FIG. 10A.

In this preparation, it appeared that the polymerization of the poly (lactic acid) occurred at a rate comparable to that at which it reacted with phosphatidylethanolamine. Minimization of this side-reaction could be achieved by using more dilute solutions of the reactants.

D. Preparation of polyglycolic acid amide of DSPE

A mixture of 266 mg. (3.50 mmoles) glycolic acid, 745 mg (3.60 mmoles) dicyclohexyl carbodiimide, 75 mg. (0.10 mmoles) distearoyl phosphatidyl ethanolamine, 32 microliters (0.23 mmoles triethyl amine, and 5.0 ml dry dimethyl sulfoxide was heated at 75° C., under a nitrogen atmosphere, cooled to room temperature, then diluted with an equal volume of chloroform, and then washed with three successive equal volumes of water to remove dimethyl sulfoxide. Phases were centrifuged and separated with a Pasteur pipette each time.

The chloroform phase was filtered under reduced pressure to remove a small amount of suspended material. The filtrate was then evaporated under vacuum to dryness to obtain 572 mg. pale amber wax. This material was redissolved in 2.5 ml chloroform and transferred to the top of a 21 mm×270 mm column of silica gel (Merck Hieselgel 60) previously wetted with chloroform.

The chromatogram was developed by passing through the column, in sequence, 100 ml each of:

100% chloroform, 0% (1% $NH_4OH$ in methanol);
90% chloroform, 10% (1% $NH_4OH$ in methanol);
85% chloroform, 15% (1% $NH_4OH$ in methanol);
80% chloroform, 20% (1% $NH_4OH$ in methanol);
70% chloroform, 30% (1% $NH_4OH$ in methanol).

Individual 25 ml portions of effluent were collected and assayed by TLC on $Si)_2$-coated plates, using $CH Cl_3$, $CH_3OH$, $H_2O$, con-$NH_4OH$; 130, 70, 8, 0.5 v/v as developer. Almost all of the PO4—positive material was found in the 275–300 ml portion of effluent. Evaporation of this portion to dryness under vacuum, followed by high-vacuum drying, afforded 281 mg of colorless wax. Phosphate analysis of the wax confirmed a molecular weight of 924,000. This material was used to produce polyglycolic acid-PE-containing liposomes used in experiments summarized in FIG. 10A.

Manipulation of solvent volume during reaction and molar ratios of glycolic acid and dicyclohexyl carbodiimide produces compounds having different molecular weights.

E. Preparation of Polyglycolic/Polylactic acid amide of PE

The same synthetic approach detailed above can be applied to the preparation of random polylactic/polyglycolic copolymers chemically linked to PE by an amide bond. In this case, equimolar quantities of distearoyl phosphatidyl ethanolamine and a 1-to-1 mixture of polyglycolic acid, polylactic acid are mixed with a three-fold molar excess of dicyclohexyl carbodiimide and a two-fold molar excess of triethylamine in a sufficient volume of dimethyl sulfoxide to dissolve all components at 75° C. The reaction is allowed to proceed 48 hours under an inert atmosphere. The product is purified by column chromatography as described above for the polylactic and polyglycolic amides of PE.

F. Preparation of polyvinyl alcohol carbamate of PE

Ten grams of 50,000 molecular weight polyvinyl alcohol (PVA) were dissolved in 200 ml water by heating. The solution was cooled to 45° C. and filtered. The solution was then mixed with an equal volume of acetone, and the resulting solid precipitate removed by filtration (Whatman #1). A low molecular weight (MW) PVA fraction was recovered from the filtrate by evaporation of the solvent. A yield of 920 mg was obtained.

PE was reacted with carbonyl diimidazole (CDI) in the presence of triethylamine (TEA) at a molar ratio of 1:1.1:1 (PE:CDI:TEA) in benzene at 75° C. for 4 hours. A low molecular weight fraction of PVA, prepared as detailed above, was then added (0.1μ per mole of PE) and the reaction was continued at 75° C. for 24 hours. The resulting PVA-PE was used to prepare liposomes which were used in experiments summarized in FIG. 10B.

EXAMPLE 3

Preparation of Ethylene-Linked PEG-PE

A. Preparation of I-trimethylsilyloxy-polyethylene glycol

Preparation of I-trimethylsilyloxy-polyethylene glycol is illustrated in the reaction scheme shown in FIG. 3.

15.0 gm (10 mmoles) of polyethylene glycol M.Wt. 1500, (Aldrich Chemical) was dissolved in 80 ml benzene. 1.40 ml (11 mmoles) of chlorotrimethyl silane (Aldrich Chemical Co.) and 1.53 ml (1 mmoles) of triethylamine was added. The mixture was stirred at room temperature under an inert atmosphere for 5 hours.

The mixture was filtered with suction to separate crystals of triethylammonium chloride and the crystals were washed with 5 ml benzene. Filtrate and benzene wash liquids were combined. This solution was evaporated to dryness under vacuum to provide 15.83 grams of colorless oil which solidified on standing.

TLC of the product on Si-$C_{18}$ reversed-phase plates using a mixture of 4 volumes of ethanol with 1 volume of water as developer, and iodine vapor visualization, revealed that all the polyglycol 1500 ($R_f$=0.93) was consumed, and was replaced by a material of $R_f$=0.82. An infra-red spectrum revealed absorption peaks characteristic only of polyglycols.

Yield of I-trimethylsilyoxypolyethylene glycol, M.W. 1500 was nearly quantitative.

B. Preparation of trifluoromethane sulfonyl ester of I-trimethylsilyloxy-polyethylene glycol 15.74 grams (10 mmol) of the crystalline I-trimethylsilyloxy polyethylene glycol obtained above was dissolved in 40 ml anhydrous benzene and cooled in a bath of crushed ice. 1.53 ml (11 mmol) triethylamine and 1.85 ml (11 mmol) of trifluoromethanesulfonic anhydride obtained from Aldrich Chemical Co. were added and the mixture was stirred over night under an inert atmosphere until the reaction mixture changed to a brown color.

The solvent was then evaporated under reduced pressure and the residual syrupy paste was diluted to 100.0 ml with methylene chloride. Because of the great reactivity of trifluoromethane sulfonic esters, no further purification of the trifluoromethane sulfonyl ester of I-trimethylsilyloxy polyethylene glycol was done.

C. Preparation of N-1-trimethylsilyloxy polyethylene glycol 1500 PE 10 ml of the methylene chloride stock solution of the trifluoromethane sulfonyl ester of 1-trimethylsilyloxy polyethylene glycol was evaporated to dryness under vacuum to obtain about 1.2 grams of residue (approximately 0.7 mmoles). To this residue, 3.72 ml of a chloroform solution containing 372 mg (0.5 mmoles) egg PE was added. To the resulting solution, 139 microliters (1.0 mmole) of triethylamine was added and the solvent was evaporated under vacuum. To the obtained residue, 5 ml dry dimethyl formamide and 70 microliters (0.50 mmoles) triethylamine (VI) was added. Air from the reaction vessel was displaced with nitrogen. The vessel was closed and heated in a sand bath a 110° C. for 22 hours. The solvent was evaporated under vacuum to obtain 1.58 grams of brownish colored oil.

A 21×260 mm chromatographic absorption column filled with Kieselgel 60 silica 70–230 mesh, was prepared and rinsed with a solvent composed of 40 volumes of butanone, 25 volumes acetic acid and 5 volumes of water. The crude product was dissolved in 3 ml of the same solvent and transferred to the top of the chromatography column. The chromatogram was developed with the same solvent and sequential 30 ml portions of effluent were assayed each by TLC.

The TLC assay system used silica gel coated glass plates, with solvent combination butanone/acetic acid/water; 40/25/5; v/v/v. Iodine vapor absorption served for visualization. In this solvent system, the N-1-trimethylsilyloxy polyethylene glycol 1500 PE appeared at $R_f$=0.78. Unchanged PE appeared at $R_f$=0.68.

The desired N-1-trimethylsilyloxy polyethylene glycol 1500 PE was a chief constituent of the 170–300 ml portions of column effluent. When evaporated to dryness under vacuum these portions afforded 111 mg of pale yellow oil of compound.

D. Preparation of N-polyethylene glycyl 1500: phosphatidyl-ethanolamine acetic acid deprotection Once-chromatographed, PE compound was dissolved in 2 ml of tetrahydrofuran. To this, 6 ml acetic acid and 2 ml water was added. The resulting solution was let to stand for 3 days at 23° C. The solvent from the reaction mixture was evaporated under vacuum and dried to constant weight to obtain 75 mg of pale yellow wax. TLC on Si-C18 reversed—phase plates, developed with a mixture of 4 volumes ethanol, 1 volume water, indicated that some free PE and some polyglycol-like material formed during the hydrolysis.

The residue was dissolved in 0.5 ml tetrahydrofuran and diluted with 3 ml of a solution of ethanol water; 80:20; v:v. The mixture was applied to the top of a 10 mm×250 mm chromatographic absorption column packed with octadecyl bonded phase silica gel and column was developed with ethanol water 80:20% by volume, collecting sequential 20 ml portions of effluent. The effluent was assayed by reversed phase TLC. Fractions containing only product of Rf=0.08 to 0.15 were combined. This was typically the 20–100 ml portion of effluent. When evaporated to dryness, under vacuum, these portions afforded 33 mg of colorless wax PEG-PE corresponding to a yield of only 3%, based on the starting phosphatidyl ethanolamine.

NMR analysis indicated that the product incorporated both PE residues and polyethylene glycol residues, but that in spite of the favorable-appearing elemental analysis, the chain length of the polyglycol chain has been reduced to about three to four ethylene oxide residues. The product prepared was used for a preparation of PEG-PE liposomes.

E. Preparation of N-Polyethylene glycol 1500 P.E. by fluoride deprotection 500 mg of crude N-1-trimethylsilyloxy polyethylene glycol PE was dissolved in 5 ml tetrahydrofuran and 189 mg (0.600 millimoles) of tetrabutyl ammonium fluoride was added and agitated until dissolved. The reactants were let to stand over night at room temperature (20° C.).

The solvent was evaporated under reduced pressure and the residue was dissolved in 10 ml chloroform, washed with two successive 10 ml portions of water, and centrifuged to separate chloroform and water phases. The chloroform phase was evaporated under vacuum to obtain 390 mg of orange-brown wax, which was determined to be impure N-polyethylene glycol 1500 PE compound.

The wax was re-dissolved in 5 ml chloroform and transferred to the top of a 21×270 mm column of silica gel moistened with chloroform. The column was developed by passing 100 ml of solvent through the column. The Table 2 solvents were used in sequence:

TABLE 2

| Volume % Chloroform | Volume % Methanol Containing 2% Conc. Ammonium Hydrloxide/Methanol |
|---|---|
| 100% | 0% |
| 95% | 5% |
| 90% | 10% |
| 85% | 15% |
| 80% | 20% |
| 70% | 30% |
| 60% | 40% |
| 50% | 50% |
| 0% | 100% |

Separated 50 ml fractions of column effluent were saved. The fractions of the column were separated by TLC on Si-C18 reversed-phase plates. TLC plates were developed with 4 volumes of ethanol mixed with 1 volume of water. Visualization was done by exposure to iodine vapor.

Only those fractions containing an iodine-absorbing lipid of $R_f$ about 0.20 were combined and evaporated to dryness under vacuum and dried in high vacuum to constant weight. In this way 94 mg of waxy crystalline solid was obtained of M.W. 2226. The proton NMR spectrum of this material dissolved in deuterochloroform showed the expected peaks due to the phosphatidyl ethanolamine portion of the molecule, together with a few methylene protons attributable to polyethylene glycol. (Delta=3.7).

EXAMPLE 4

Preparation of REVs and MLVs

A. Sized REVs

A total of 15 μmoles of the selected lipid components, in the mole ratios indicated in the examples below, were dissolved in chloroform and dried as a thin film by rotary evaporation. This lipid film was dissolved in 1 ml of diethyl ether washed with distilled water. To this lipid solution was added 0.34 ml of an aqueous buffer solution containing 5 mM Tris, 100 mM NaCl, 0.1 mM EDTA, pH 7.4, and the mixture was emulsified by sonication for 1 minute, maintaining the temperature of the solution at or below room temperature. Where the liposomes were prepared to contain encapsulated [$^{125}$I] tyraminyl-inulin, the compound was included in the phosphate buffer at a concentration of about 4 μCi/ml buffer.

The ether solvent was removed under reduced pressure at room temperature, and the resulting gel was taken up in 0.1 ml of the above buffer, and shaken vigorously. The resulting REV suspension had particle sizes, as determined by microscopic examination, of between about 0.1 to 20 microns, and was composed predominantly of relatively large (greater than 1 micron) vesicles having one or only a few bilayer lamellae.

The liposomes were extruded twice through a polycarbonate filter (Szoka, 1978), having a selected pore size of 0.4 microns or 0.2 microns. Liposomes extruded through the 0.4 micron filter averaged 0.17± (0.05) micron diameters, and through the 0.2 micron filter, 0.16 (0.05) micron diameters. Non-encapsulated [$^{125}$I] tyraminyl-inulin was removed by passing the extruded liposomes through Sephadex G-50 (Pharmacia).

B. Sized MLVs

Multilamellar vesicle (MLV) liposomes were prepared according to standard procedures by dissolving a mixture of lipids in an organic solvent containing primarily $CHCl_3$ and drying the lipids as a thin film by rotation under reduced pressure. In some cases a radioactive label for the lipid phase was added to the lipid solution before drying. The lipid film was hydrated by addition of the desired aqueous phase and 3 mm glass beads followed by agitation with a vortex and shaking above the phase transition temperature of the phospholipid component for at least 1 hour. In some cases a radioactive label for the aqueous phase was included in the buffer. In some cases the hydrated lipid was repeatedly frozen and thawed three times to provide for ease of the following extrusion step.

For use in lung localization experiments, MLVs were produced by one of the two specific methods described below.

MLV Method 1. Multilamellar vesicles were prepared by hydrating either of two solid lipid mixture forms: thin film or lyophilized tertbutanol solution. Lipid mixtures were prepared with one or more of the following: partially hydrogenated egg phosphatidylcholine (PHEPC) with an iodine value of 40 (Asahi Chemical, Japan) hydrogenated soy phosphatidylcholine (HSPC) (Avanti Polar Liposomes, Birmingham, Ala.), USP grade cholesterol (C) (Croda), N-carbamyl-poly (ethylene glycol methyl ether)-1,2-distearyl-sn-glycero-3-phospho-ethanolamine, sodium salt (MPEG-1900-DSPE) (Chemsyn, Lenexa, Kans.). Thin films of lipids were hydrated by shaking with the component. The resulting liposomes dispersions were frozen and thawed three times before further processing. Lyophilized lipid mixtures were hydrated by shaking with the aqueous phase as above. Extrusion was performed under high pressure in a stainless steel cell (MICO, Middleton, Wis.) through successively smaller defined pore filters until a pore size of 0.05 μm diameter was reached (Nucleopore, Pleasanton, Calif.) or a mean particle diameter of less than or equal to 100 nm. The particle size distribution was determined by dynamic light scattering (Coulter N4SD). Phospholipid concentrations were measured by phosphorus determination (Barlett, 1959). In some cases, the lipids were hydrated by slowly pouring ethanol lipid solutions into an aqueous solution above the phase transition temperature of the phospholipid component and shaking for 60 min. These dispersions were homogenized with a Rannie Minilab-8 (St. Paul, Minn.) above the phase transition temperature of the phospholipid component at pressures sufficient to give a mean particle diameter of less than or equal to 100 nm. In one case, the homogenization pressure was reduced to yield a sample with a mean particle diameter of 150 nm.

In the experiments described herein PEG-containing liposomes typically had a composition comprising PEG-DSPE:HSPC:Cho=0.15:1.85:1, representing a PEG-DSPE content of 5 mole percent, unless otherwise indicated.

MLV Method 2. Hydrogenated soybean phosphatidylinositol (HPI), hydrogenated soybean phosphatidylcholine (HPC), egg phosphatidylglycerol (PG) and egg phosphatidylcholine (PC) were obtained from Avanti Polar Lipids Inc. (Alabaster, Ala.) Cholesterol (Chol) was from Sigma Chemical (St. Louis, Mo.). $^{67}$Ga-citrate and $^{111}$In-chloride were from Frosst (Quebec, Canada). Deferoxamine mesylate (DF) was from Ciba-Geigy (Basel, Switzerland). The acetate form of AG1X2 resin (acetate form, 200–400 mesh) was from Bio-Rad (Richmond, Calif.).

Liposomes were prepared consisting of either HPI-HPC-Chol or PG-PC-Chol both in a molar ratio 1:10:5. A chloroform/methanol (9:1, v/v) solution of the lipid mixture was evaporated to dryness in a round bottom flask. The lipids were redissolved in 2 ml of cyclohexane and lyophilized. Multilamellar vesicles containing desferoxamine (DF) were formed by vortex mixing of the lipid film in a buffer solution containing 10 mM Hepes, 150 mM NaCl and 25 mM DF (pH 7.4). Lipid concentration was 100 $\mu$mol/ml. Vortex mixing was performed for twelve 20-sec. periods at room temperature or, in the case of HPI-HPC-Chol liposomes at 62° C. Liposomes were extruded 10 times through polycarbonate filters of 0.05 $\mu$m pore size (Nucleopore Corp.; Pleasanton, Calif.), using an extruder device from Lipex Biomembranes (Vancouver, Canada). For sizing of the HPI-HPC-Chol liposomes the extruder device was pre-heated to 62° C. Liposomes were separated from non-entrapped DF by delfiltration on a Sephadex G-50 column (Pharmacia, Uppsala, Sweden) with 10 mM Hepes and 150 mM Na C; (pH 7.4) as the elution buffer. Phospholipid concentration was determined by phosphate assay. Mean particle size was determined by dynamic light scattering (Malvern 4700 system, Malvern, UK). As a measure of the particle size distribution of the dispersion the system reports a polydispersity index. This index ranges from 0.0 for a monodisperse sample up to 1.0 for a completely polydisperse sample. The mean particle size of the liposomes used was 100±4 with a polydispersity index of 0.13±0.02 (mean±SD of 9 preparations) for the HPI-HPC-Chol liposomes, and 110±9 nm with a polydispersity index of 0.21±0.07 (mean±SD of 3 preparations) for the PG-PC-Chol liposomes. Maximum storage time of liposomes was 24 h at 4° C. under nitrogen. The liposomes were radiolabeled with $^{67}$Ga-deferoxamine ($^{67}$Ga-DF) as described below.

As described above, the size of the liposome samples was controlled by extrusion through defined pore polycarbonate filters using pressurized nitrogen gas. In one procedure, the liposomes were extruded one time through a filter with pores of 0.4 $\mu$m and then ten times through a filter with pores of 0.1 $\mu$m. In another procedure, the liposomes were extruded three times through a filter with 0.2 $\mu$m pores followed by repeated extrusion with 0.05 $\mu$m pores until the mean diameter of the particles was below 100 nm as determined by DLS. Unencapsulated aqueous components were removed by passing the extruded sample through a gel permeation column separating the liposomes in the void volume from the small molecules in the included volume.

C. Loading $^{67}$Ga-DF into Liposomes

The protocol for preparation of Ga$^{67}$-DF labeled liposomes as adapted from known procedures (Gabizon, 1988–1989). Briefly, REV or MLV liposomes were prepared as described above. The ion chelator desferal mesylate (DF) was encapsulated in the internal aqueous phase of the liposomes and used to irreversibly trap $^{67}$Ga-DF in the liposome.

$^{67}$Ga-citrate for injection (Neoscan, NEN Cambridge Mass.) is supplied as a 2 mCi/ml solution. Conversion of the citrate chelate to a bilayer permeable oxide chelate (hydroxyquinoline) was performed by diluting the Ga-citrate stock 1:10 with 5 mg/ml hydroxyquinoline sulfate (Sigma Chemical Co.) in 0.9% saline for injection and heating to 50° C. for 1 hr. The heating step was performed on a 1–2 ml solution in a capped and sealed 15 ml conical test tube in a lead shipping container placed on a hot plate and filled with about 2 ml of water. After heating, the Ga-oxide stock solution was allowed to cool and stored at room temperature in a lead shipping container.

For $^{67}$Ga-DF loading of liposomes, samples were hydrated with 5 mM desferoxamine mesylate (DF, Sigma Chemical, St. Louis, Mo.) in 0.9% saline for injection at 100 $\mu$M phospholipid/ml and homogenized. Unentrapped DF was removed by either dialysis or gel permeation chromatography through an anion exchange resin (AG1X2). Dialysis was performed against 0.9% saline for injection. Gel permeation chromatography was performed on columns pre-equilibrated with 0.9% saline for injection. Then the samples were mixed 10:1 with the Ga-oxide solution and then capped, mixed, and incubated at 4° C. Loading with 0.1–3 $\mu$Ci/$\mu$M lipid gave good results. Unentrapped Ga label was removed by either dialysis or gel chromatography.

D. Determination of Liposome Particle Size Distribution by Dynamic Light Scattering Liposome particle size distribution measurements were obtained by DLS using a NICOMP Model 200 with a Brookhaven Instruments BI-2030AT autocorrelator attached, or as described above. The instruments were operated according to the manufacturer's instructions. The NICOMP results were expressed as the mean diameter and standard deviation of a Gaussian distribution of vesicles by relative volume.

EXAMPLE 5

Liposome Blood Lifetime Measurements

A. Measuring Blood Circulation Time and Blood/RES Ratios

In vivo studies of liposomes were performed in two different animal models: Swiss-Webster mice at 25 g each and laboratory rats at 200–300 g each. The studies in mice involved tail vein injection of liposome samples at 1 $\mu$M phospholipid/mouse followed by animal sacrifice after a defined time and tissue removal for label quantitation in a scintillation counter. The weight and percent of the injected dose in each tissue were determined. The studies in rats involved establishment of a chronic catheter in a femoral vein for removal of blood samples at defined times after injection of liposome samples in a catheter in the other femoral artery at 3–4 $\mu$M phospholipid/rat. In general, rat studies were carried out using $^{67}$Ga-DF loaded liposomes and radioactivity was measured using a gamma counter. The percent of the injected dose remaining in the blood at several time points up to 24 hours, and in selected tissues at 24 hours, was determined.

B. Time Course of Liposome Retention in the Bloodstream

PEG-PE composed of methoxy PEG, molecular weight 1900 and 1-palmitoyl-2-oleyl-PE (POPE) was prepared as in Example 2. The PEG-POPE lipid was combined with and partially hydrogenated egg PC (PHEPC) in a lipid:lipid mole ratio of about 0.1:2, and the lipid mixture was hydrated and extruded through a 0.1 micron polycarbonate membrane, as described in Example 4, to produce MLV's with average size about 0.1 micron. The MLV lipids included a small amount of radiolabeled lipid marker $^{14}$C-cholesteryl oleate, and the encapsulated marker either $^{3}$H-inulin or $^{67}$Ga-DF as described in Example 4.

The liposome composition was injected and the percent initial injected dose in mice was determined as described in Example 4, at 1, 2, 3, 4, and 24 after injection. The time course of loss of radiolabeled material is seen in FIG. 7 which is a plot of percent injected dose for encapsulated inulin (solid circles), inulin marker corrected to the initial injection point of 100% (open circles), and lipid marker (closed triangles), over a 24-hour period post injection. As seen, both lipid and encapsulated markers showed greater than 10% of original injected dose after 24 hours.

C. 24 Hour Blood Liposome Levels

Studies to determine percent injected dose in the blood, and blood/RES ratios of a liposomal marker, 24 hours after intravenous liposome injection, were carried out as described above. Liposome formulations having the compositions shown at the left in Table 3 below were prepared as described above. Unless otherwise noted, the lipid-derivatized PEG was PEG-1900, and the liposome size was 0.1 micron. The percent dose remaining in the blood 24 hours after intravenous administration, and 24-hour blood/RES ratios which were measured are shown in the center and right columns in the table, respectively.

TABLE 3

|  | 24 Hours after IV Dose | |
|---|---|---|
| Lipid Composition* | % Injected Dose in Blood | B/RES |
| PG:PC:Chol (.75:9.25:5) | 0.2 | 0.01 |
| PC:Chol (10:5) | 0.8 | 0.03 |
| PEG-DSPE:PC:Chol | 23.0 | 3.0 |
| PEG-DSPE:PC:Chol (250 nm) | 9.0 | 0.5 |
| PEG$_{5000}$-DSPE:PC:Chol | 21.0 | 2.2 |
| PEG$_{120}$-DSPE:PC:Chol | 5.0 | 2.0 |
| PEG-DSPE:PC (0.75:9.25) | 22.0 | 0.2 |
| PEG-DSPE:PG:PC:Chol (0.75:2.25:7:5) | 40.0 | 4.0 |
| PEG-DSPE:NaCholSO$_4$:PC:Chol (0.75:0.75:9.25:4.25) | 25.0 | 2.5 |

*All formulations contain 33% cholesterol and 7.5% charged component and were 100 nm mean diameter except as noted. PEG-DSPE consisted of PEG$_{1900}$ except as noted. Liposome distribution and kinetics were followed using encapasulated $^{67}$Ga-DF as a label. Rates were injected IV as described in Example 4.

As seen, percent dose remaining in the blood 24 hours after injection ranged between 5–40% for liposomes containing PEG-derivatized lipids. By contrast, in both liposome formulations lacking PEG-derivatized lipids, less than 1% of liposome marker remained after 24 hours. Also as seen in Table 3, blood/RES ratios increased from 0.01–0.03 in control liposomes to at least 0.2, and as high as 4.0 in liposomes containing PEG-derivatized liposomes.

D. Blood lifetime measurements with polylactic acid derivatized PE

Figure 10A:
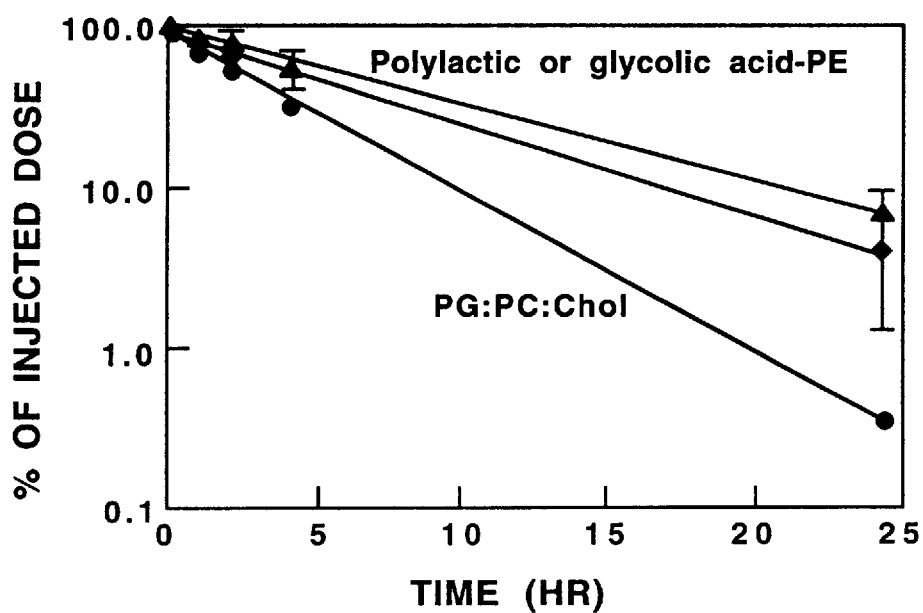
FIG. 10A is a plot similar to that of FIG. 7, showing the blood residence time of polylactic or polyglycolic acid-coated liposomes (upper line) and conventional uncoated liposomes (lower line)

Studies to determine percent injected dose in the blood at several times after intravenous liposome injection were carried out as described above. Typical results with extruded MLV liposome formulation having the composition Polylactic Acid-PE:HSPC:Chol at either 2:3.5:1 or 1:3.5:1 weight % is shown in FIG. 10A (solid squares). The percent dose remaining normalized at 15 min. is shown over 24 hours.

These data indicate that the clearance of the polylactic acid-coated liposomes is severalfold slower than similar formulations without polylactic acid derivatized PE.

E. Blood lifetime measurements with polyglycolic acid Derivatized PE

Studies to determine percent injected dose in the blood at several times after intravenous liposome injection were carried out as described above. Typical results with extruded MLV liposome formulation having the composition Polyglycolic Acid-PE:HSPC:Chol at 2:3.5:1 weight % are shown in FIG. 10A (open triangles). The percent dose remaining normalized at 15 min. is shown over 24 hours.

These data indicate that the clearance of the polyglycolic acid-coated liposomes is severalfold slower than similar formulations without polyglycolic acid derivatized PE.

F. Blood Lifetime Measurements with Polyvinyl Alcohol PE

Figure 10B:
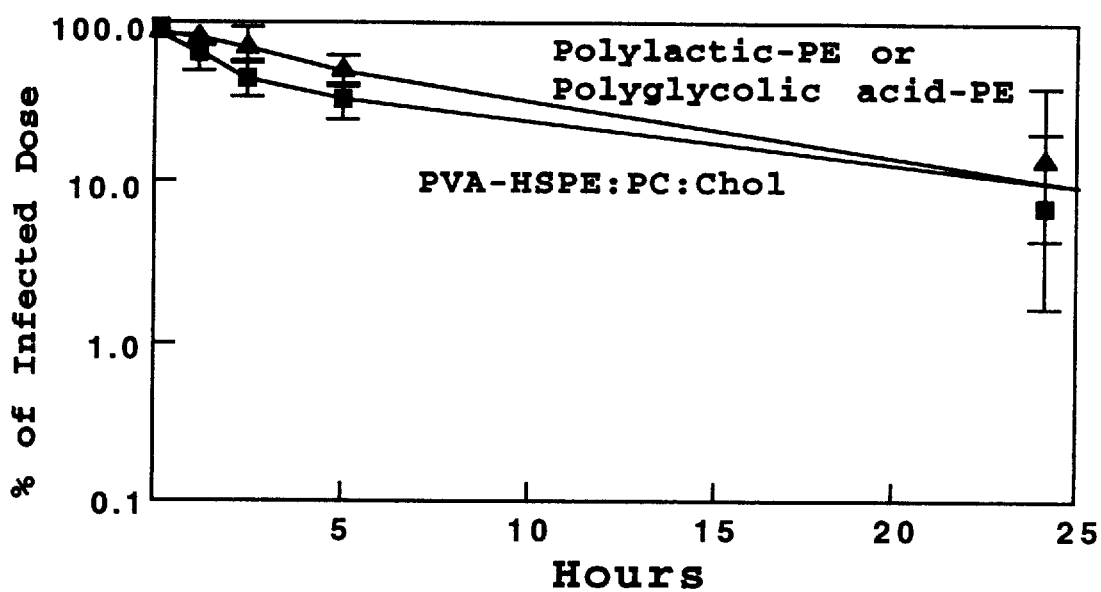
FIG. 10B is a plot similar to that of FIG. 7, showing the blood residence time of polylactic or polyglycolic acid-coated liposomes (upper line) and polyvinyl acid-coated liposomes (lower line)

Studies to determine percent injected dose in the blood at several times after intravenous liposome injection were carried out as described above. Typical results with extruded MLV liposome formulation having the composition Polyvinyl alcohol-HSPE:PC:Chol at either 2:3.5:1 or 1:3.5:1 weight % is shown in FIG. 10B in comparison to the results of polylactic acid- and polyglycolic acid-derivatized liposomes described in Sections E and F, above. The percent dose remaining normalized at 15 min. is shown over 24 hours. The results for blood residence time of polyvinyl alcohol-derivatized liposomes are similar to results obtained for polylactic acid- and polyglycolic acid-derivatized species, as described above. These data indicate that the clearance of the polyvinyl alcohol-coated liposomes is severalfold slower than similar formulations without polyvinyl alcohol derivatized PE.

EXAMPLE 6

Effect of Phospholipid Acyl-Chain Saturation on Blood/RES Ratios in PEG-PE Liposomes PEG-PE composed of methoxy PEG, molecular weight 1900 and distearylPE (DSPE) was prepared as in Example 2. The PEG-PE lipids were formulated with selected lipids from among sphingomyelin (SM), fully hydrogenated soy PC (PC), cholesterol (Chol), partially hydrogenated soy PC (PHSPC), and partially hydrogenated PC lipids identified as PC IV1, IV10, IV20, IV30, and IV40 in Table 4. The lipid components were mixed in the molar ratios shown at the left in Table 5, and used to form MLV's sized to 0.1 micron as described in Example 4.

TABLE 4

| Egg PC Form | Phase Transition Temperature Range °13 C. | Mole % Fatty Acid Comp. | | | | | | |
|---|---|---|---|---|---|---|---|---|
| | | 18:0 | 18:1 | 18:2 | 20:0 | 20:1–4 | 22:0 | 22:1–6 |
| Native | <0 | 12 | 30 | 15 | 0 | 3 | | 05 |
| IV 40 | <0 | 14 | 32 | 4 | 0 | 3 | | 04 |
| IV 30 | <20–30 | 20 | 39 | 0 | 1 | 2 | | 34 |
| IV 20 | 23–45 | 30 | 10 | 0 | 2 | 1 | | 33 |
| IV 10 | 37–50 | 42 | 4 | 0 | 3 | 1 | | 42 |
| IV 1 | 49–54 | 56 | 0 | 0 | 5 | 0 | | 60 |

TABLE 5[a]

| | Blood | RES | B/RES | % Remaining |
|---|---|---|---|---|
| PEG-PE:SM:PC:Chol 0.2:1:1:1 | 19.23 | 6.58 | 2.92 | 49.23 |
| PEG-PE:PHSPC:Chol 0.15:1.85:1 | 20.54 | 7.17 | 2.86 | 55.14 |
| PEG-PE:PC IV1:Chol 0.15:1.85:1 | 17.24 | 13.71 | 1.26 | 60.44 |
| PEG-PE:PC IV1:Chol (two animals) 0.15:1.85:1 | 19.16 | 10.07 | 1.90 | 61.87 |
| PEG-PE:PC IV10:Chol (two animals) 0.15:1.85:1 | 12.19 | 7.31 | 1.67 | 40.73 |
| PEG-PE:PC IV10:Chol 0.15:1.85:1 | 2.4 | 3.5 | 0.69 | [b]12.85 |
| PEG-PE:PC IV20:Chol 0.15:1.85:1 | 24.56 | 7.52 | 3.27 | 62.75 |
| PEG-PE:PC IV40:Chol 0.15:1.85:1 | 5.2 | 5.7 | 0.91 | [b]22.1 |
| PEG-PE:PC IV40:Chol 0.15:1.85:1 | 19.44 | 8.87 | 2.19 | 53.88 |
| PEG-PE:PC IV:Chol 0.15:1.85:0.5 | 20.3 | 8.8 | 2.31 | 45.5 |
| PEG-PE:EPC:Chol 0.15:1.85:1 | 15.3 | 9.6 | 1.59 | 45.9 |

[a]Groups of at least 3 mice were used per experiment except where otherwise noted and $^{67}$Ga-DF was used to follow the liposomes.
[b]Values with low recoveries (i.e., <40%) are considered unreliable.

Twenty-four hours after injection, the percent material injected (as measured by percent of $^{67}$Ga-DF) remaining in the blood and in the liver (L) and spleen (S) were determined, and these values are shown in the two data columns at the left in Table 5. The blood and L+S (RES) values were used to calculate a blood/RES value for each composition. The column at the right in Table 5 shows total amount of radioactivity recovered. The two low total recovery values in the table indicate anomalous clearance behavior.

The results from the table demonstrate that the blood/RES ratios are largely independent of the fluidity, or degree of saturation of the phospholipid components forming the liposomes. In particular, there was no systematic change in blood/RES ratio observed among liposomes containing largely saturated PC components (e.g., IV1 and IV10 PC's), largely unsaturated PC components (IV40), and intermediate-saturation components (e.g., IV20).

In addition, a comparison of blood/RES ratios obtained using the relatively saturated PEG-DSPE compound and the relatively unsaturated PEG-POPE compound (Example 5) indicates that the degree of saturation of the derivatized lipid is itself not critical to the ability of the liposomes to evade uptake by the RES.

EXAMPLE 7

Effect of Cholesterol and Ethoxylated Cholesterol on Blood/RES Ratios in PEG-PE Liposomes A. Effect of added cholesterol Methoxy PEG, molecular weight 1900 and was derivatized with DSPE as described in Example 2. The PEG-PE lipids were formulated with selected lipids from among sphingomyelin (SM), fully hydrogenated soy PC (PC), and cholesterol (Chol), as indicated in the column at the left in Table 6 below. The three formulations shown in the table contain about 30, 15, and 0 mole percent cholesterol. Both REV's (0.3 micron size) and MLV's (0.1 micron size) were prepared, substantially as in Example 4, with encapsulated tritium-labeled inulin.

The percent encapsulated inulin remaining in the blood 2 and 24 hours after administration, given at the left in Table 6 below, show no measurable effect of cholesterol, in the range 0–30 mole percent.

TABLE 6

| | % Injected Dose in Blood | | | |
|---|---|---|---|---|
| | 2 hr. | 24 hr. | 2 hr. | 24 h. |
| $^3$H-Inulin | $^3$H Aqueous Label (Leakage) | | $^{14}$C-Lipid Label | |
| SM:PC:Chol:PEG-DSPE 1:1:1:0.2 | | | | |
| 100 nm MLV | 19 | 5 | 48 | 24 |
| 300 nm REV | 23 | 15 | 67 | 20 |
| SM:PC:Chol:PEG-DSPE 1:1:0.5:0.2 | 23 | 15 | 71 | 17 |
| 300 nm REV | | | | |
| SM:PC:PEG-DSPE 1:1:0.2 | | | | |
| 100 nm MLV | 19 | 6 | 58 | 24 |
| 300 nm REV | 32 | 23 | 76 | 43 |

B. Effect of ethoxylated cholesterol

Methoxy-ethoxy-cholesterol was prepared by coupling methoxy ethanol to cholesterol via the trifluorosulfonate coupling method described in Section I. PEG-PE composed of methoxy PEG, molecular weight 1900 and was derivatized DSPE as described in Example 2. The PEG-PE lipids were formulated with selected lipids from among distearyl-PC (DSPC), partially hydrogenated soy PC (HSPC), cholesterol, and ethoxylated cholesterol, as indicated at the left in Table 7. The data show that (a) ethoxylated cholesterol, in combination with PEG-PE, gives about the same degree of enhancement of liposome lifetime in the blood as PEG-PE alone. By itself, the ethoxylated cholesterol provides a moderate degree of enhancement of liposome lifetime, but substantially less than that provided by PEG-PE.

TABLE 7

| | % Injected Dose in Blood $^{14}$C-Chol-Oleate | |
|---|---|---|
| Formulation | 2 hr. | 24 hr. |
| HSPC:Chol:PEG-DSPE 1.85:1:0.15 | 55 | 9 |
| HSPC-Chol:PEG-DSPE:PEG$_5$-Chol 1.85:0.85:0.15:0.15 | 57 | 9 |
| HSPC:Chol:HPC:PEG$_5$-Chol 1.85:0.85:0.15:0.15 | 15 | 2 |
| HSPC:Chol:HPG 1.85:1:0.15 | 4 | 1 |

EXAMPLE 8

Effect of Charged Lipid Components on Blood/ RES Ratios in PEG-PE Liposomes

Methoxy PEG, molecular weight 1900 was derivatized with DSPE as described in Example 2. The PEG-PE lipids were formulated with lipids selected from among egg PG (PG), partially hydrogenated egg PC (PHEPC), and cholesterol (Chol), prepared as MLV's, sized to 0.1 micron as in Example 4. The two liposomal formulations were used in experiments summarized in FIG. 7, where liposomes containing about 4.7 mole percent (triangles) or 14 mole percent (circles) were compared.

The percent of injected liposome dose present 0.25, 1, 2, 4, and 24 hours after injection are plotted for both formulations in FIG. 7. As seen, the percent PG in the composition had little or no effect on liposome retention in the bloodstream. The rate of loss of encapsulated marker seen is also similar to that observed for similarly prepared liposomes containing no PG.

EXAMPLE 9

Plasma Kinetics of PEG-Coated and Uncoated Liposomes

Methoxy PEG, molecular weight 1900 and distearylPE (DSPE) were prepared as in Example 2. The PEG-PE lipids were formulated with PHEPC, and cholesterol, in a mole ratio of 0.15:1.85:1. A second lipid mixture contained the same lipids, but without PEG-PE. Liposomes were prepared from the two lipid mixtures as described in Example 5, by lipid hydration in the presence of desferal mesylate, followed by sizing to 0.1 micron, and removal of non-entrapped desferal by gel filtration with subsequent loading of $^{67}$Ga-oxide into the liposomes. The unencapsulated $^{67}$Ga was removed during passage through a Sephadex G-50 gel exclusion column. Both compositions contained 10 μmoles/ml in 0.15 M NaCl, 0.5 mM desferal.

The two liposome compositions (0.4 ml) were injected IV in animals, as described in Example 6. At time 0.25, 1, 3 or 5 and 24 hours after injection, blood samples were removed and assayed for amount inulin remaining in the blood, expressed as a percentage of the amount measured immediately after injection. The results are shown in FIG. 8B. As seen, the PEG-coated liposomes have a blood halflife of about 11 hours, and nearly 30% of the injected material is present in the blood after 24 hours. By contrast, uncoated liposomes showed a halflife in the blood of less than 1 hour. At 24 hours, the amount of injected material was undetectable (FIG. 8B).

EXAMPLE 10

Culture of infectious microorganisms
A. *Klebsiella pneumoniae*

*K. pneumoniae* (ATCC 43816, capsular serotype 2) cultures were obtained by incubation of cells for 16 hours at 37° in Iso-Sensitest broth (Oxoid LTD., London, Great Britain). Following dilution and re-incubation for 2 h, suspensions of logarithmically growing bacteria were prepared for injection into animals.

EXAMPLE 11

Infection of Rats with bacterial pathogen

Female R strain albino rats (specific pathogen-free, 14–18 weeks old; 185–215 g; Source, ITRI-TNO, Rkjswijk, The Netherlands). Rats were anesthetized with fluanisone (Hypnorm®, Duphar B. V., Amsterdam, The Netherlands) and pentobarbital (Abbott Laboratories, North Chicago, Ill.). The left main stem bronchus was intubated, and the left lung was inoculated with 0.02 ml. saline suspension containing $10^5$ CFU of *K. pneumoniae*. Following infection, Nalorphine bromide (Onderlinge Pharmaceutische Groothandel, Utrecht), an opiate antagonist, was given to the animal by injection.

To measure severity of infection, animals were sacrificed, and the left and right lungs removed separately, weighed and homogenized in 20 ml of phosphate-buffered saline (PBS) for 30 sec at 10,000 rpm in a VirTis homogenizer (The VirTis Co., Gardiner, N.Y.). Serial ten-fold dilutions of homogenates were prepared. Volumes of 0.2 ml of each dilution as well as 1 ml volumes of the undiluted lung homogenate were spread on bloodagar plates for quantitation of bacteria. Quantitation of numbers of bacteria in the left (infected) and right (uninfected) lungs of treated rats, as well as increase in weight of the infected lung tissue, were used to assess severity of infection.

EXAMPLE 12

Preparation of Liposome-Drug Formulations
A. Loading Gentamicin Sulfate into Liposomal Preparation Liposomes were prepared by thin film hydration as described in Example 4 using gentamicin sulfate concentrations from 20 to 100 mg/ml, and total lipid concentrations from 50 to 300 μmole/ml. Experiments testing these liposomes identified practical limits of ≦50 mg/ml for gentamicin and ≦150 μmole/ml for lipid. Above these concentrations, non-liposomal particles were formed. Further studies showed that hydration of a lipid cake formed by lyophilization from tert-butanol with aqueous gentamicin sulfate was preferable in terms of apparent homogeneity of the initial dispersion and ease of subsequent down-sizing by extrusion. Lyophilized lipid cake hydration was further tested using 1000 μmoles lipid. This amount of lipid was hydrated in a final volume of 10 ml giving 50 mg/ml gentamicin and 100 μmoles lipid/ml.

The extent of gentamicin sulfate loading, using liposomes formed by the lipid cake hydration method, was determined after gel chromatography through either with G-25 in a syringe or an A15M column. These results (Table 8) represent loading of liposomes before removal of unentrapped drug. In the experiment shown hydration of liposomes was carried out by addition of 10 ml of isotonic gentamicin solution and 100 μmol lipid/ml. Hydration was carried out, using the gentamicin in water followed by dilution with saline before 2-step method.

TABLE 8

Characterization of Gentamicin Sulfate Samples Before Free Drug Removal

| Sample ID # | Hydration Method[1] Gentamicin SO$_4$ | Input Drug/Lipid Ratio μg/μmole | Percent Loading[2] (Method) | Calculated Bound Drug Lipid Ratio μg/μmole | Mean Diameter After Extr. nm |
|---|---|---|---|---|---|
| 634-84 | 2-step | 500(N) | 50(D) | 250 | 92 |
| 634-91 | " | 500(N) | 35(D) | 175 | 98 |
| 634-95 | 1-step | 500(N) | 14(D) | 70 | 90 |
| 665-5 | " | 500(N) 340 | 13 | 65(N) 44 | 92 |
| 665-10A | " | 500(N) 794 | 9 | 45(N) 71 | 95 |

TABLE 8-continued

Characterization of Gentamicin Sulfate Samples Before Free Drug Removal

| Sample ID # | Hydration Method[1] Gentamicin SO$_4$ | Input Drug/Lipid Ratio µg/µmole | Percent Loading[2] (Method) | Calculated Bound Drug Lipid Ratio µg/µmole | Mean Diameter After Extr. nm |
|---|---|---|---|---|---|
| 665-10B | " | 500(N) | 11 | 55(N) | 96 |
| 665-10C | 2-step (overnight) | 500(N) 565 | 15 20(D) | 75(N) 85 | 96 |
| 665-6 | 1-step (5 mM DF) | 500(N) | 8 | 40(N) | 94 |
| 665-16C | 1-step (5 mM DF) | 500(N) 538 | 10 | 50(N) 54 | 91 |
| 665-16H | 1-step (glucose) | 500(N) | 8.4 | 40(N) | 98 |
| 665-16E | Heated 100 mg/mL 200 µmole/ml | 500(N) | —[3] | | |
| 665-16G (20 mL) | 2-step 25 mg/ml 50 µmole/ml | 500(N) | 7.4 | 35(N) | 106 |
| 665-16A | 1-step 10 mg/ml | 100(N) | 12 | 12(N) | 86 |
| 665-16B | 1-step 100 mg/ml | 1000(N) 1137 | 7.6 | 70(N) 80 | 96 |
| 665-16D | Heated 200 mg/ml 200 µmole/ml | 1000(N) | — | | |
| 665-16F (20 ml) | 2-step 50 mg/ml 50 µmole/ml | 1000(N) | 8.8 | 88(N) | 96 |
| 665-59A | 100 mg/ml diluted late | 1000(N) | 7.4 | 74(N) | 93 |
| 665-59B | 100 mg/ml diluted early | 1000(N) | 4.0 | 40(N) | 97 |
| 665-73B | 100 mg/ml diluted late & stood | 1000(N) | 9 | 90(N) | 128 |

[1]Standard condition: 50 mg/ml gentamicin, 100 µmole/ml lipid, isotomic saline, 1000 µmoles lipid, 10 ml.
[2](D) = Dialysis, (G-25) = small syringe method, Otherwise Biogel A15M; (N) = Nominal value;
[3]— either the pressure required for extrusion exceeded 900 psi or excessive foaming occurred.
[3](N): Nominal value, based on input ratio of components; all other values based on determinations made on final products.

The results of variations in the lipid composition are shown in Table 9. As shown, only small differences in the amount of drug associated with the liposomes were observed using the lipid composition variations shown. At a 500 µg/µmole input drug/lipid ratio, the amount of drug bound by or associated with the lipid was usually near or above the minimum considered acceptable, 50 µg/µmole lipid, indicating an efficiency of about 10%.

TABLE 9

Effect of Lipid Composition on S-Gentamicin Sulfate Loading

| Sample ID # | Hydration Method[1] Gentamicin SO$_4$ | Input Drug/Lipid Ratio µg/µmole | Percent Loading[2] (Method) | Calculated Bound Drug Lipid Ratio µg/µmole | Mean Diameter After Extr. nm |
|---|---|---|---|---|---|
| 665-43B | 1-step (No Chol) | 500(N) | 11 | 55(N) | 90 |
| 665-28 | 2-step 10% Peg | 500(N) | 9.3 | 45(N) | 112 |
| 665-41A | 1-step (+5% NaCSO$_4$) | 500(N) | 9.2 | 45(N) | 93 |
| 665-41B | 1-step (+15% NaCSO$_4$) | 500(N) | 10 | 57.5(N) | 94 |

[1]Standard condition: 50 mg/ml gentamicin, 100 µmole/ml lipid, isotomic saline, 1000 µmoles lipid, 10 ml.
[2](D) = Dialysis, (G-25) = small syringe method, Otherwise Biogel A15M; (N) = Nominal value;
[3]—, either the pressure required for extrusion exceeded 900 psi or excessive foaming occurred.

Table 10 shows results of experiments in which the effects of variation of particle size on drug loading was investigated. Increasing particle size gave only a small increase in the amount of bound drug (Table 10). Increasing the drug/lipid ratio present during liposome formation by a factor of two increased the level of bound drug disproportionally, as exemplified by sample 16B. Decreasing the drug/lipid by a factor of 5 increased the efficiency somewhat and gave a considerably reduced bound drug/lipid ratio. All these results were obtained at a nominal lipid concentration of 100 μmoles/ml.

TABLE 10

Effect of Particle Size on S-Gentamicin Sulfate Loading

| Sample ID # | Particle Size | Drug/Lipid Ratio | Percent Loading (Method)* | Calculated Bound Drug Lipid |
|---|---|---|---|---|
| 634-84 | 65 | 500(N) | 50(D) | 250(N) |
|  | 130 | 500(N) | 50(D) | 250(N) |
| 656-16C | 91 | 500(N) | 10 | 50(N) |
|  | 126 | 500(N) | 12.5 | 63(N) |
| 665-16A | 86 | 100(N) | 12 | 12(N) |
|  | 105 | 100(N) | 14 | 14(N) |
| 665-16B | 86 | 1000(N) | 7.6 | 70(N) |
|  | 128 | 1000(N) | 7.5 | 75(N) |
| 665-59A | 93 | 1000(N) | 7.4 | 74(N) |
|  | 137 | " | 9.4 | 94(N) |
| 665-59B | 97 | " | 4.0 | 40(N) |
|  | 133 | " | 4.6 | 46(N) |
| 665-43B | 90 | 500(N) | 11.0 | 55(N) |
|  | 120 | 500(N) | 12.7 | 64(N) |
| 665-41A | 93 | 500(N) | 9.2 | 45(N) |
|  | 129 | 500(N) | 10 | 50(N) |
| 665-41B | 94 | 500(N) | 10 | 58(N) |
|  | 127 | 500(N) | 12 | 58(N) |

*(D) = Dialysis, Otherwise Biogel A15M
(N) = Nominal value

B. Loading of Gentamicin Chloride into Liposomes

Gentamicin chloride was prepared by precipitation of sulfate from a gentamicin sulfate formulation, by addition of $BaCl_2$. Recovery of 90% of the gentamicin was achieved. Liposomal gentamicin preparations were prepared by hydration of lyophilized cakes of lipid using gentamicin chloride solutions, as summarized in Table 11. Hydration with 25 mg/ml gentamicin chloride of 100 μmole/ml lipid gave 18% loading before free drug removal. Substitution of cholesterol sulfate for free cholesterol gave 24% loading (sample 43C). Increasing the particle size gave a slight increase in loading before cleanup.

TABLE 11

Characterization of S-Gentamicin Chloride Samples Before Free Drug Removal

| Sample ID # | Hydration[1] Method | Input Drug/Lipid Ratio | Percent[2] Loading (Method)* | Calculated Bound Drug Lipid |
|---|---|---|---|---|
| 56B | STD | 500(N) | 11 | 54 |
| 51B | pH 3 | 500(N) | 6.2 | 31 |
| 16J | in Salt | 500(N) | 15 | 73 |
| 43A | - Chol | 500(N) | 13 | 63 |
| 63 | - Chol/Salt (Large) | 500(N) | 14 | 70 |
| 42A | 15% Na $CSO_4$ | 500(N) | 17 | 87 |
| 42B | 15% Na $CSO_4$ pH 3 (Large) | 500(N) | 18 | 90 |
| 43C | 33% Na $CSO_4$ | 500(N) | 24 | 120 |

TABLE 11-continued

Characterization of S-Gentamicin Chloride Samples Before Free Drug Removal

| Sample ID # | Hydration[1] Method | Input Drug/Lipid Ratio | Percent[2] Loading (Method)* | Calculated Bound Drug Lipid |
|---|---|---|---|---|
| 56A | 100 mg/ml (Large) | 1000(N) | 13 | 130 |
| 56C | 100 mg/ml Salt (Large) | 1000(N) | 14 | 140 |
| 16I | Glucose 200 μmole/ml | 250(N) | 19 | 48 |
| 51A | 25 mg/ml | 250(N) | 18 | 44 |
| 51C | 25 mg/ml 200 μmole/ml | 125(N) | 10 | 13 |

[1]Standard method consisted of the following: 50 mg/ml gentamicin Cl prepared in isotonic glucose at pH 5; 100 μmole/ml total lipid, PEG-DSPE:PHEPC:C; one step hydration of lyophilized lipid cake at room temp. The $NaCSO_4$ was substituted for some or all of the C in these samples. Large indicates that extrusion to a particle size ≦100 was not possible and the results with a ~150 nm particle size sample are reported.
[2]By A-15M gel column in saline.

C. PEG-DSPE-containing Liposomes

MLV-liposome gentamicin formulations were prepared by hydrating a cake of lipids lyophilized from tert-butanol with an aqueous solution of gentamicin containing trace amounts of $^{125}$I-gentamicin. Mole ratios of the lipid mixtures used to form the liposomes were as follows: MPEG-1900-DSPE:PHEPC:Cho, 5:62:33 (corresponding to S mole % PEG-derivatized DSPE). The final concentration of gentamicin and lipid before extrusion were typically 50 mg/ml and 100 μmoles total lipid/ml, respectively. Variations in these parameters are reported with the results obtained. The hydrated liposome dispersion was repeatedly extruded through defined pore filters (Nucleopore).

D. Removal of Unbound Gentamicin

Following hydration and formation of liposomal suspensions, unbound drug was removed. Dialysis against a non-drug containing solution, such as sterile saline was carried out in some cases. However, for gentamicin solutions, it was found that removal of gentamicin was incomplete even after a dialysis time of 48 hours (Table 12 —sample 665-6).

Ion exchange resin Dowex AG50v was used to effect batch or column removal of free drug using standard methods. In order to remove free drug using the batch method, two treatments with AG50v were generally required.

Gel permeation was evaluated using BioRad 10DG or Sephadex G-50 (Pharmacia, Piscataway, N.J.) columns, where BioRad 10DG columns are used for relatively small sample volumes. The G-50 method of drug removal followed by concentration showed excellent resolution (FIG. 17) and a high percentage of bound gentamicin. This method is a preferred method of removal of unbound gentamicin.

TABLE 12

Characterization of Gentamicin Sulfate Samples After Free Drug Removal

| Sample ID # | Method of Free Drug Removal | Total Gent. Conc. mg/ml | Total Lipid Conc. μmole/ml | Percent Entrapped (Biogel A-15M) | Bound Drug/Lipid Ratio μg/mole | pH ColorpHast (0–14) |
|---|---|---|---|---|---|---|
| 634-84 | dialysis | 7 | 87 | 75 | 60 | ND |
| 634-91 | " | 8 | 86 | 77 | 72 | ND |
| 634-95 | " | 5 | 74 | 39 | 27 | ND |
| 665-5 | Bio-10DG | 3.4 | 125 | 80 | 22 | ND |
| 665-10A | Bio-10DG | 2.6 | 92 | 69 | 20 | ND |
| 665-10C | Dialysis | 6.8 | ND | 50 | ND | ND |
| 665-10C | G-50 | 1 | 42 | 97 | 23 | 5.5 |
| 665-6 | dialysis | 4 | 80 | 45 | 23 | ND |
| 665-6 | 2nd dialysis | ND | ND | 86 | ND | ND |
| 665-16C + 665-6 | G-50 | 1.6 | 50 | 99 | 32 | ND |
| 665-16H | G-50 | 2.3 | 68 | 96 | 20.7 | 5.5 |
| 665-16G (20 ml) | G-50 | 1.0 | 54 | 95 | 17.6 | 5.5 |
| 665-16B | G-50 | 1.8 | 44 | 98 | 41 | 5.5 |
| 665-16F (20 ml) | G-50 | 1.0 | 63 | 58 | 9.3 | 5.5 |
| 665-59A | Bio-10DG | 2.0 | 56 | 78 | 27.6 | ND |
| 665-59B | Bio-10DG | 1.8 | 30 | 84 | 17.5 | ND |
| 665-73B | Bio-10DG | 1.5 | NA* | ~80 | NA | ND |
| 665-43B | G-50 | 3.2 | 37 | 83 | 71.4 | ND |
| 665-28 | G-50 | 1.8 | 78 | 68 | 16 | 6 |

*Data Not Available

Table 13 shows drug to lipid ratios achieved with gentamicin chloride after removal of unbound drug. In general, the results show about twice the drug/lipid ratio achieved with gentamicin sulfate. With several conditions, levels of 50 to 70 μg/μmole were achieved. Elimination of cholesterol, or its substitution with cholesterol sulfate improved the drug loading. A lower pH inhibited the loading.

For most experiments, removal of unentrapped gentamicin was performed by gel permeation chromatography with Sephadex G-50 either with a column 2.5×45 cm or 1.25×25 cm. Samples of up to 20 ml (⅓ the void volume) were applied to the larger column and up to 5 ml to the smaller one. Unentrapped drug was eluted before reuse of the column. The samples were concentrated by repeated centrifugation in a Centriprep 10 centrifuge (Aminco, Danvers Mass.) at 3000 rpm in a Sorval T-60 rotor (1600xg) for 30 min. to 1 h.

TABLE 13

Characterization of S-Gentamicin Chloride Samples After Free Drug Removal

| Sample ID # | Particle Size | Percent Loading *(Method) | Calculated Bound Drug Lipid | Method | [Gent.] | [Lipid] | Percent Entrap. | Bound Drug to Lipid Ratio |
|---|---|---|---|---|---|---|---|---|
| 56B | 92 | 11 | 54 | G-50 | 0.6 | 30 | 69 | 14 |
|  | 140 |  |  | 10DG | 1.5 | 72 | 58 | 12 |
| 51B | 150 | 6.2 | 31 | G-50 | 0.8 | 28 | 68 | 19 |
| 16J | 128 | 14.5 | 72.5 | G-50 | 4.3 | 40 | 40 | 43 |
|  | 144 | 15.5 | 77.5 | 10DG | 1.9 | 31 | 54 | 34 |
| 43A | 104 | 12.6 | 63 | 10DG | 2.1 | 30 | 63 | 44 |
|  | 138 | 14.3 | 71.5 | 10DG | 2.3 | 32 | 68 | 49 |
| 42A | 92 | 17.3 | 86.5 |  | 2.0 | 30 | 78 | 52 |
|  | 134 | 19.9 | 99.5 | 10DG | 1.5 | 17 | 62 | 54 |
| 43C | 95 | 24.1 | 121 | G-50 | 1.4 | 17 | 84.5 | 73 |
|  | 128 | 24.6 | 123 | 10DG | 2.7 | 17 | 75.6 | 122 |
| 56A | 167 | 13 | 130 | 10DG | 2.7 | 29 | 54 | 52 |
| 56C | 157 | 14 | 140 | 10DG | 8.9 | 30 | 40 | 119 |
| 16I | 132 | 19 | 47.5 | G-50 | 1.1 | 26 | 72 | 31 |
|  | 153 | 35 |  | 10DG | 1.9 | 48 | 67 | 27 |
| 51A | 94 | 18 | 44 | G-50 | 1.0 | 18 | 49 | 29 |
| 51C | 90 | 10 | 13 | G-50 | 0.4 | 28 | 60 | 23 |
|  | 147 | 17.3 | 22 | G-50 | 0.8 |  | 83 |  |

E. Drug-Liposome Formulations for In Vivo Studies the liposomal gentamicin formulations were characterized by measurements of particle size, lipid concentration, and pH by standard methods as described above. Gentamicin incorporation was determined by inclusion of tracer $^{125}$I-labeled gentamicin (NEN, Cambridge, Mass.) or by reaction with trinitrobenzene sulfonate (TNBS) as described below in Example 13.

The amount of gentamicin bound to the liposomes was determined by gel permeation chromatography using Bio-Rad A-15M resin. Samples of 200 to 300 µl were loaded onto a column of 0.5×30 cm equilibrated and eluted with saline. Fractions were collected and the amount of gentamicin which eluted with the liposomes in the void volume of the column was determined by amount of $^{125}$I present. The percentage of liposomal gentamicin was determined from the ratio of the label eluting in the void volume to the total label eluting.

TABLE 14

Determination of Percent Liposomal Incorporation of Gentamicin

| Sample | Method | Percent Incorporated | Notebook Reference |
|---|---|---|---|
| 634-84 | G-25 syringe | 68% | 656:62; 70–71 |
| 634-84 | A15M | 75% | 656:73–74 |
| 634-95 | G-25 syringe | 43% | 656:66 |
| 634-95 | A-15M | 39% | 656:66 |
| 634-98 | G-25 syringe | 51% | 656:67 |
| 634-98 | A-15M | 45% | 656:67 |

EXAMPLE 13

Localization of liposomes in infected tissue

A. Localization of $^{67}$Ga-containing liposomes

PEG-derivatized MLV liposomes were prepared as detailed in Example 4, using a ratio of PEG-DSPE:PHEPL IV40:CHO of 0.15:1.85:1. Liposomes used in liposome localization studies were prepared by one of two procedures. In the first, lipids were dissolved in a solution of 50% ethanol. Saline solution containing 5 mM desferal mesylate was added to the mixture with stirring at room temperature. The mixture was homogenized to produce liposomes having an average diameter of 95 or 147 nm. These liposomes were loaded with $^{67}$Ga, as described in Example 4 prior to injection.

The second procedure used to prepare MLV $^{67}$Ga-loaded liposomes for use in localization to infected regions was similar to that described in Example 4 as MLV method 1. Lipids were dissolved in chloroform ($CHCl_3$) and dried as a thin film on the surface of a round bottom evaporation flask, in the presence of 3 mm glass beads under reduced pressure. After removal of residual solvent, lipids were hydrated by addition of a solution containing 5 mM desferal and 5% (wt/vol) glucose at 600° followed by vortex mixing and mixing on a wrist shaker for 45 min. The mixture was alternately frozen (dry ice/ethanol) and thawed three times, then extruded through a polycarbonate filter having a pore size of 0.2 µm, followed by extrusion through a filter having a pore size of 0.08 µm. Resulting liposomes had a average diameter of 79 nm. The liposomes were loaded with $^{67}$Ga, as described in Example 4 prior to injection.

Rats were infected with K. pneumoniae as described in Example 11. Forty-eight hours later, each rat was injected with 5, 10, 15, 20 or 25 µmol $^{67}$Ga liposomes contained in a volume of 0.9 ml, and blood samples were taken by retroorbital puncture under $CO_2$ anesthesia to quantitate circulating liposome levels. Liposome blood circulation time and liposome content of liver, spleen, left lung (one lobe), right lung (four lobes) and liver was assessed using the high affinity 67Ga-desferal complex as marker. Correction for blood content of the tissues was performed using $^{111}$In-oxide-labelled syngeneic erythrocytes (Heaton) injected intravenously 10 minutes prior to dissection of tissues. Radioactivity was quantitated in a γ-counter (Minaxy 5530, Packard Instruments Co., Downers Grove, U.S.A.). Encapsulated $^{67}$Ga served as a marker to determine the distribution of intact liposomes in the various tissues. Forty hours following injection, approximately 10% of the injected liposomes were circulating in the blood. Localization of liposomes in lung tissue was determined in a group of 31 rats having varying levels of infection (infected lung bacterial levels: $10^5$–$2 \times 10^{10}$, weight of infected left lung: 0.45–2.2 gram). Results of these studies are illustrated in FIGS. 12, 13, 14, 15A, 15B, 16A and 16B.

B. Localization of gentamicin-containing liposomes in infected tissues

Gentamicin sulfate was loaded into PEG containing liposomes as detailed above in Example 12. Gentamicin-loaded liposomes were injected intravenously (15 µmol lipid) into rats infected with Klebsiella 48 hours earlier by intubation and instillation of the inoculum to one lung, as detailed in Example 11. Blood levels and accumulation of drug in the infected tissue were measured by assay of tissues for gentamicin content, as described in Example 13, above. Alternatively, accumulation of gentamicin was measured by determination of radioactive content of infected lung, when the liposomal gentamicin formulation included trace levels of radiolabeled gentamicin. Results of studies in which accumulation of gentamicin was measured in infected lung tissue are shown in FIGS. 18A and 18B.

EXAMPLE 14

Stability of PEG-derivatized, Gentamicin Liposomes

Several lots of PEG-derivatized liposomes containing gentamicin sulfate were prepared by the cake hydration method detailed above and summarized as follows: 1000 µmole lipid cakes were hydrated with 2.5 ml of gentamicin sulfate at 200 mg/ml in water by shaking for 1 hr, then diluted to 10 ml with isotonic saline giving 50 mg/ml gentamicin sulfate and 100 µmoles lipid/ml. The dispersions were extruded to give a mean particle size less than 100 nm. The unentrapped drug was removed by gel chromatography and the total volume reduced by centrifugation in a Centriprep-10 concentrator. These compositions were stored at 8° C. and assayed over the course of two weeks (Table 15) for liposome associated (entrapped) gentamicin, by pelleting the liposomes at 200,000×g in 7×20 mm centrifuge tubes for 60 minutes, followed by assaying for gentamicin as described in Example 13. The results indicate that the drug to lipid ratio achieved after cleanup with G-50 Sephadex can be maintained even in clean samples (see samples 665-16H and 16G, Table 15).

TABLE 15

Stability of Cleaned Gentamicin Sulfate Liposomes

| Time (Day) | Sample ID | Percent Entrapped (Bio-gel A-15M) | Particle Size (90° angle) nm | pH |
|---|---|---|---|---|
| 0 | 665-16G | 95 | 91 | 5.5 |
| 11 | | 88 | 99 | 5.0 |
| 20 | | 84 | 102 | |
| 2 | *665-16F | 58 | 100 | 5.5 |
| 6 | | 55 | 101 | 5.0 |
| 2 | *665-16H | 96 | 96 | 5.5 |

TABLE 15-continued

Stability of Cleaned Gentamicin Sulfate Liposomes

| Time (Day) | Sample ID | Percent Entrapped (Bio-gel A-15M) | Particle Size (90° angle) nm | pH |
|---|---|---|---|---|
| 6 | | 94 | 96 | 5.0 |
| 15 | | 92 | 99 | |
| 2 | *665-28 | 68 | 110 | 6.0 |
| 6 | | 69 | 109 | 5.0 |

*Sample cleaned on Day 0 but not concentrated or assayed until Day 2.

EXAMPLE 15

Kinetics & Tissue Distribution of Gentamicin-loaded PEG-containing Liposomes FIG. 18A shows the results of studies in which rats were infected in the left lung with K. pneumoniae at time=0, as described in Example 11, then injected 24 hours later (Time=24) with an intravenous dose of 15 mg/kg gentamicin sulfate (open circles), 1.9 mg/kg gentamicin sulfate PEG-containing liposomes having cholesterol in the formulation (closed circles), or 1.9 mg/kg gentamicin sulfate PEG-containing liposomes lacking cholesterol (closed triangles). $^{125}$I-gentamicin was included in the gentamicin formulations. Gentamicin content of the infected lungs was assessed by measurement of radioactivity present in the infected tissue at the time points indicated. FIG. 18B shows the same data expressed as percent of total injected dose.

EXAMPLE 16

Therapeutic Activity of Gentamicin-loaded PEG-containing Liposomes

Table 16 shows and summarizes the results of experiments in which rats were infected with K. pneumoniae in the left lung, as described in Example 11, then injected 48 hours later with 1.9 or 15 mg/kg gentamicin sulfate, as indicated, or with a PEG-containing liposomal preparation of gentamicin sulfate. Two different liposomal compositions were used. One composition (PEG:PC:CH) contained cholesterol (CH), while the other composition (PEG:PC) lacked cholesterol. The first three rows of each time point shown in Table 16 contain log values of colony forming units (CFU) of bacteria isolated from the infected lungs of three individual rats at each time point, where 48 hours is the time of injection of gentamicin. The fourth row of each time point contains the mean log CFU value±one standard deviation, for the three measurements.

TABLE 16

| time in hours | PBS | Free 15 mg/kg | PEG:PC:CH 1.9 mg/kg | PEG:PC 1.9 mg/kg | Free 1.9 mg/kg |
|---|---|---|---|---|---|
| 48 | 8.7 | | | | |
| | 8.5 | | | | |
| | 6.6 | | | | |
| | 7.9 ± 1.16 | | | | |
| 52 | | 9.3 | 7.3 | 8.5 | 8.0 |
| | | 4.7 | 7.8 | 8.6 | 5.7 |
| | | 8.7 | 8.1 | 8.1 | 9.3 |
| | | 7.6 ± 2.50 | 7.7 ± 0.40 | 8.4 ± 0.26 | 7.7 ± 1.82 |
| 72 | 9.7 | 4.5 | 6.7 | 7.4 | 8.7 |
| | 7.4 | 9.5 | 7.9 | 8.8 | 9.7 |
| | 7.6 | 9.0 | 8.2 | 8.9 | 9.4 |
| | 8.2 ± 1.27 | 7.7 ± 2.70 | 7.6 ± 0.79 | 8.4 ± 0.84 | 9.3 ± 0.51 |
| 76 | | 7.4 | 7.6 | 8.4 | 7.5 |
| | | 7.7 | 7.0 | 8.2 | 6.8 |
| | | 7.5 | 7.4 | | 8.8 |
| | | 7.5 ± 0.15 | 7.3 ± 0.31 | | 7.7 ± 1.01 |
| 96 | | 6.7 | 5.8 | 7.7 | 6.8 |
| | | 5.6 | 4.5 | 7.7 | 9.8 |
| | | 7.7 | 4.6 | | 7.8 |
| | | 6.6 ± 1.05 | 5.0 ± 0.72 | | 8.1 ± 1.53 |
| 120 | | 6.0 | | 7.5 | |
| | | 6.9 | | | |
| | | 3.8 | | | |
| | | 5.6 ± 1.59 | | | | not available.

FIG. 19 shows the results of a similar experiment in which rats were infected at time=0, then given gentamicin either as free drug (1.9 mg/kg, open circles) or as a liposomal composition (1.9 mg/kg) 24 hours later.

Although the invention has been described and illustrated with respect to particular derivatized lipid compounds, liposome compositions, and use, it will be apparent that a variety of modifications and changes may be made without departing from the invention.

It is claimed:

1. A method of treating a systemic infection which is localized at a site other than the fixed macrophages residing in the liver or the spleen, comprising administering to the subject, by intravenous injection, a composition of liposomes (i) composed of vesicle-forming lipids, including 1–35 mole percent of a diacyl-chain amphipathic vesicle-forming lipid derivatized with polyethylene glycol having a molecular weight between about 350 and 5,000 daltons (ii) having a selected mean particle diameter in the size range between about 0.07–0.20 microns, and (iii) containing in liposome-entrapped form, a therapeutic compound effective against the source of the infection, and by said injecting, achieving at least about a ten-fold increase in the concentration of liposomes in the infected tissue over that achievable by the such liposomes in the absence of the amphipathic vesicle-forming lipid derivatized with said polyethylene glycol.

2. The method of claim 1, wherein the infection is bacterial in origin and the therapeutic compound is an antibiotic.

3. The method of claim 2, wherein at least about 60% of the antibiotic agent is in liposome-entrapped form.

4. The method of claim 1, wherein the antibiotic agent is an aminoglycoside antibiotic, the concentration of which entrapped in the liposomes is greater than 20 μg compound/μmole liposome lipid.

5. The method of claim 1, wherein the infection site is lung, the source of the infection is Klebsiella, and the therapeutic agent is gentamicin.

* * * * *